United States Patent
Westphal et al.

(10) Patent No.: US 12,343,542 B2
(45) Date of Patent: Jul. 1, 2025

(54) INDIRECT SENSING MECHANISM FOR CARDIAC MONITORING

(71) Applicant: Medtronic Bakken Research Center B.V., Maastricht (NL)

(72) Inventors: Philip Westphal, Maastricht (NL); Richard N. Cornelussen, Maastricht (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 384 days.

(21) Appl. No.: 17/653,615

(22) Filed: Mar. 4, 2022

(65) Prior Publication Data
US 2022/0296906 A1  Sep. 22, 2022

Related U.S. Application Data

(60) Provisional application No. 63/163,607, filed on Mar. 19, 2021.

(51) Int. Cl.
| | | |
|---|---|---|
| *A61N 1/365* | (2006.01) | |
| *A61B 5/00* | (2006.01) | |
| *A61B 5/021* | (2006.01) | |
| *A61B 5/11* | (2006.01) | |
| *G16H 50/20* | (2018.01) | |
| *G16H 50/70* | (2018.01) | |

(52) U.S. Cl.
CPC .......... *A61N 1/36578* (2013.01); *A61B 5/021* (2013.01); *A61B 5/1107* (2013.01); *A61B 5/686* (2013.01); *A61B 5/7264* (2013.01); *A61N 1/36585* (2013.01); *G16H 50/20* (2018.01); *G16H 50/70* (2018.01); *A61B 2562/0219* (2013.01)

(58) Field of Classification Search
CPC ............ A61N 1/36578; A61N 1/36585; A61N 1/37211; A61N 1/39–1/3993; A61N 1/3712; A61B 5/021; A61B 5/1107; A61B 5/686; A61B 2562/0219; A61B 5/6869; A61B 5/72–5/7296; G16H 50/20; G16H 50/70
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |
| | (Continued) | |

OTHER PUBLICATIONS

International Search Report and Written Opinion of International Application No. PCT/EP2022/056611, dated Jun. 20, 2022, 16 pp.
(Continued)

*Primary Examiner* — Jonathan T Kuo
(74) *Attorney, Agent, or Firm* — Shumaker & Sieffert, P.A.

(57) ABSTRACT

This disclosure is directed to systems and techniques for detecting change in patient health based upon patient data. In some examples, a medical system includes a mechanosensor configured to sense a first physiological parameter signal of a patient; and processing circuitry configured to: determine one or more features of the first physiological parameter signal; apply a machine leaning model to the one or more features of the first physiological parameter signal; and based on the application of the machine learning model, determine an estimated value of a second physiological parameter.

17 Claims, 10 Drawing Sheets

(56) References Cited

U.S. PATENT DOCUMENTS

| | | | |
|---|---|---|---|
| 5,545,182 | A | 8/1996 | Stotts et al. |
| 5,755,736 | A | 5/1998 | Gillberg et al. |
| 9,586,052 | B2* | 3/2017 | Gillberg ............. A61N 1/37247 |
| 11,234,630 | B2* | 2/2022 | Peters .................... G16H 10/60 |
| 2008/0288013 | A1 | 11/2008 | Schecter |
| 2015/0038856 | A1* | 2/2015 | Houlton ............... A61B 5/6826 |
| | | | 600/484 |
| 2016/0045744 | A1* | 2/2016 | Gillberg ............. A61N 1/36842 |
| | | | 607/9 |
| 2020/0288990 | A1 | 9/2020 | Remme |
| 2021/0378537 | A1* | 12/2021 | Peters ................... A61B 5/332 |

OTHER PUBLICATIONS

Yli-Ollila et al., "Principal Component Analysis of the Longitudinal Carotid Wall Motion in Association with Vascular Stiffness: A Pilot Study," Ultrasound in Medicine & Biology, vol. 42, No. 12, Dec. 1, 2016, pp. 2873-2886.

\* cited by examiner

INDIRECT SENSING MECHANISM FOR CARDIAC MONITORING

PRIORITY CLAIM

This application claims the benefit of U.S. Provisional Patent Application No. 63/163,607, filed 19 Mar. 2021, the entire contents of which are incorporated herein by reference.

GOVERNMENT FUNDING

The project leading to this application has received funding from the European Union's Horizon 2020 research and innovation programme under the Marie Sklodowska-Curie grant agreement No 764738.

FIELD

The disclosure relates generally to medical systems and, more particularly, medical systems configured to monitor physiological activity for changes in patient health.

BACKGROUND

Some types of medical systems may monitor various physiological data of a patient or a group of patients to detect changes in health, e.g., to inform delivery of a therapy to improve the health of the patient. The physiological data may include, as examples, a cardiac electrogram (EGM), activity or motion, heart sounds or vibrations, oxygen saturation, and blood pressure. As an example, a medical system may monitor cardiac electromechanical function based on such physiological data, and control delivery of a therapy to improve the cardiac electromechanical function, such as cardiac resynchronization therapy (CRT), implantable cardioverter-defibrillator (ICD) therapy, or another therapy for a cardiac arrythmia.

SUMMARY

Medical systems and techniques as described herein provide real-time care in a device implanted into a patient's body, and enhance that care with monitoring mechanisms that are non-invasive with respect to the portion of the body being monitored. In one example medical system, a medical device (e.g., a pacemaker) is implanted into a patient's chest to monitor cardiac activity and, in some examples, delivers therapy to correct that patient's abnormal cardiac activity. The example medical system may define the abnormal cardiac activity with hemodynamic measurements for a cardiovascular function of interest (e.g., cardiac synchrony). The medical device (e.g., a CRT device or an ICD) may monitor cardiac electrical or mechanical activity to detect a degree of synchrony and if needed, improve the synchrony by delivering a treatment, such as a defibrillation (i.e., shock treatment) from the CRT device or the ICD. As another example, the medical device may monitor cardiac electrical or mechanical activity via hemodynamic sensing and deliver Anti-tachycardia Pacing (ATP) based on one or more criterion for certain hemodynamic measurements. In other examples, the ICD may employ hemodynamic sensing to engage in the shock treatment for life-threatening arrhythmias or sudden cardiac arrest. For both the degree of synchrony and the hemodynamic measurements, sensors enable the medical device to capture signal data for physiological parameters.

However, some physiological parameters that are particularly indicative of the above-mentioned cardiovascular function of interest, such as pressure in a heart chamber or in an artery or vein (e.g., aorta or pulmonary vein), generally require invasively positioning of sensors at locations within the left side of the heart. Some example medical devices are configured to estimate left ventricular (LV) pressure or other left side cardiac mechanical functionality measurements while other example medical devices are configured to estimate right ventricular (RV) pressure, left atrium (LA) pressure, right atrium (RA) pressure. One or more example medical devices may be configured to estimate pressure in one or more of four pulmonary veins that enter the left atrium (LA) or one or more of four coronary arteries. To minimize care involving interaction with the patient's heart, the medical device implements techniques as described herein that employ mechanisms to sense left or right side cardiac functionality, such as left ventricle pressure, that are non-invasive with respect to the left or right side of the heart.

In the present disclosure, medical devices are configured with hardware to implement various machine learning techniques for estimating a physiological parameter, such as left ventricle pressure and then, using that estimate in some functionality. In one example, a pacemaker is configured with a machine learning model (e.g., neural network, decision trees, and other artificial intelligence/machine learning algorithms) that estimates left-ventricular pressure measurements and their derivatives based on an endocardial or epicardial mechanosensory signal (e.g., accelerometer). Due to the confines and sensitivity of the human heart, the pacemaker is a relatively small device and therefore, benefits from medical systems/techniques with a low or manageable resource footprint. Given the computational complexity (or lack thereof) of the medical systems/techniques described herein, the pacemaker can implement the machine learning techniques described herein without much concern for any resource burden.

Examples of the above machine learning techniques identify a set of features from a mechanosensory signal and apply a model (e.g., as decision tree-based model) for estimating left ventricle pressure data. In the present disclosure, the model is designed and then, calibrated/trained to provide a reasonable prediction of left ventricle pressure measurements to record for current or future point-in-time. Example medical devices implementing the above machine learning techniques do not rely on directly sensing the left ventricle pressure and maintain an expected accuracy level to prevent errors, for example, when detecting/correcting abnormal cardiac rhythm. Sensor data including pressure measurements and any parameter data corresponding to a patient's left ventricle pressure that are generated by the medical systems/techniques of the present disclosure are accurate and available in real-time and automatically upon request (if so configured). In view of the above, the present disclosure describes a technological improvement or a technical solution that is integrated into a practical application.

In one example, a medical system includes a mechanosensor configured to sense a first physiological parameter signal of a patient; and processing circuitry configured to: determine one or more features of the first physiological parameter signal, apply a machine leaning model to the one or more features of the first physiological parameter signal; and based on the application of the machine learning model, determine an estimated value of a second physiological parameter.

In another example, a method includes determining one or more features of a first physiological parameter signal sensed by a mechanosensory, applying a machine leaning model to the one or more features of the first physiological parameter signal, and based on the application of the machine learning model, determining an estimated value of a second physiological parameter.

In another example, a medical system includes communication circuitry coupled, over a network, to medical device; and processing circuitry configured to: execute a training process on a corpus of cardiac activity data for a patient population or a patient sub-group; generate a machine learning model based on the training process, wherein the machine learning model is configured to use a first physiological parameter signal to determine an estimated value of a second physiological parameter; and deploy the machine learning model for use in a medical device configured to monitor cardiac activity of a patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Figure 1:
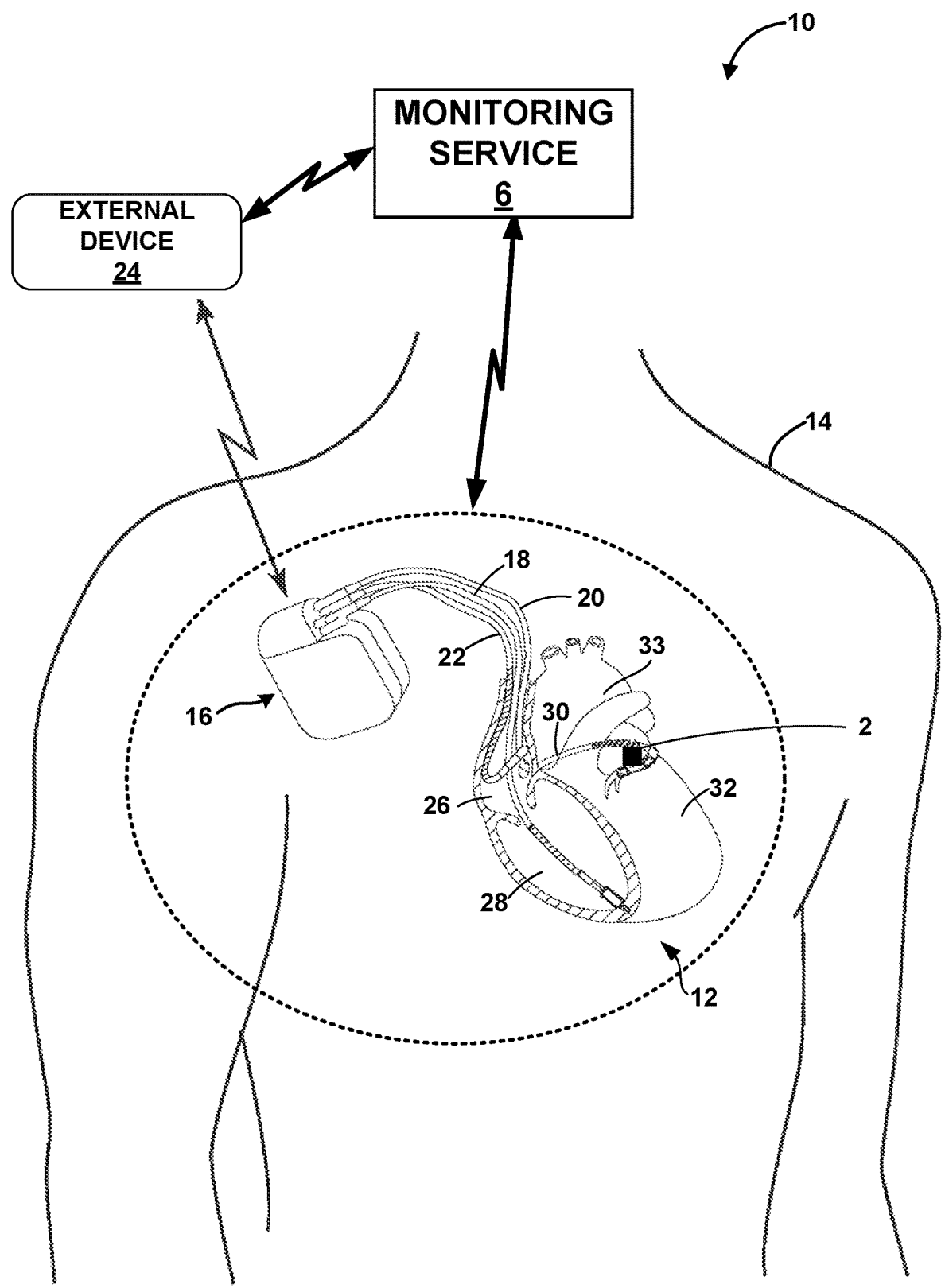
FIG. 1 illustrates example environment of an example medical system in conjunction with a patient, in accordance with one or more examples of the present disclosure.

The present disclosure describes systems and techniques to estimate certain data corresponding to a patient's heart, including his/her left ventricle chamber. The present disclosure—in which a number of implanted medical devices are described as example embodiments—introduces a mechanism to support these devices in estimating patient cardiac activity that is non-invasive with respect to the portion of the heart whose activity is estimated, such as the left ventricle. The present disclosure sets forth a solution for or an improvement to current medical devices, which often encumber difficulties when sensing portions of the patient's heart (e.g., left or right ventricle, left or right atrium, or other portions of the left or right sides of the heart).

The present disclosure, according to some examples, describes a (mathematical) model that is calibrated/trained to accurately estimate pressure data (e.g., left ventricle pressure or its derivatives) without directly sensing (e.g., measuring) that pressure data from the patient's heart. Conventional techniques that rely on direct sensing employ invasive mechanisms to acquire sensor data via the direct sensing.

Machine learning techniques (e.g., modeling techniques including a training process and an evaluation process) of which the present disclosure is directed (at least in part) to provide accurate estimates of left ventricle pressure. Some example machine learning techniques generate a decision tree-based model for the estimation, but these techniques are not restricted to that model structure and may employ other suitable models. In fact, most, if not all, model structures are applicable for the estimation. When the model is fully configured and then, sufficiently trained to estimate the left ventricular pressure and one or more derivatives, some example machine learning techniques have the model implemented into a medical device.

Implanted medical devices described herein implement the above model (e.g., in detection logic) to improve performance of device functionality and/or quality of a physician's medical care, especially if one or more of the medical device's functions would be improved by left ventricle pressure data. A pacemaker is an example of the above implanted medical devices, and accurate left ventricle pressure data may be used by the pacemaker to correct abnormal rhythms and/or improve cardiac synchrony. Instead of direct sensing, the pacemaker estimates, from mechanosensory signals, left ventricle pressure measurements within a predetermined range (e.g., of error). Because the model is sufficiently trained and then, programmed into the pacemaker, the pacemaker's estimation error may be trivial and denoted by either no performance impact or a (e.g., statistically) insignificant performance impact.

The following description is directed to a variety of medical devices (e.g., implantable devices, wearable devices, etc.) configured to monitor patient cardiac activity, detect mechanosensory signals and other input data of which at least some corresponds to a patient's left-ventricular heart chamber, and estimate a contemporaneous pressure measurement in that chamber. These medical devices implement machine learning techniques as described herein and, in some examples, function in some capacity for a medical system as described herein. To illustrate by way of example medical system, a cloud-based network device may train a model with labeled data and a learning algorithm and when the model is sufficiently trained to correctly or accurately correlate features (e.g., including captured mechanosensory signals over a period of time and to changes in left ventricle pressure.

In this manner, the systems and techniques of this disclosure may advantageously enable improved accuracy in the detection of maladies afflicting the patient and negatively affecting patient health and, consequently, better therapy and/or correction of the patient's maladies, resulting in an improved condition of the patient.

FIG. 1 illustrates example medical device system 10 in conjunction with patient 14. Medical device system 10 is an example of a medical device system that is configured to implement the example techniques described herein for estimating physiological parameter values and, in some examples, controlling the delivery of CRT to heart 12 of patient 14 based on the estimated physiological parameter values. In some examples, medical device system 10 includes an implantable medical device (IMD) 16 in communication with external device 24. In the illustrated example, IMD 16 may be coupled to leads 18, 20, and 22. IMD 16 may be, for example, an implantable pacemaker that provides electrical signals to heart 12 and senses electrical activity of heart 12 via electrodes coupled to one or more of leads 18, 20, and 22. In some examples, IMD 16 may include cardioversion and/or defibrillation capabilities.

Leads 18, 20, 22 extend into heart 12 of patient 14 to sense electrical activity of heart 12 and to deliver electrical stimulation to heart 12. In the example shown in FIG. 1, right ventricular (RV) lead 18 extends through one or more veins (not shown), the superior vena cava (not shown), and right atrium (RA) 26, and into RV 28. Left ventricular (LV) coronary sinus lead 20 extends through one or more veins, the vena cava, right atrium 26, and into the coronary sinus 30 to a region adjacent to the free wall of LV 32 of heart 12. Right atrial (RA) lead 22 extends through one or more veins and the vena cava, and into the RA 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 may also sense electrical signals attendant to the depolarization and repolarization of heart 12 via extravascular electrodes (e.g., electrodes positioned outside the vasculature of patient 14), such as epicardial electrodes, external surface electrodes, subcutaneous electrodes, and the like. The configurations of electrodes used by IMD 16 for sensing and pacing may be unipolar or bipolar.

In some examples, 1 MB 16 is configured to provide CRT to heart 12. In some examples, as part of the CRT, IMD 16 is configured to deliver at least one of fusion pacing to heart 12 and biventricular pacing to heart 12. In some examples of fusion pacing, 1 MB 16 may deliver a pacing stimulus (e.g., a pacing pulse) to LV 32 via electrodes of lead 20, where the pacing stimulus is timed such that an evoked depolarization of LV 32 is affected in fusion with the intrinsic depolarization of RV 28, resulting in a ventricular resynchronization. In this way, the pacing pulse delivered to LV 32 ($LV_P$) may pre-excite a conduction delayed LV 32 and help fuse the activation of LV 32 with the activation of RV 28 from intrinsic conduction. The fusion of the depolarization of LV 32 and RV 28 may result in synchronous activation and contraction of LV 32 with RV 28. In the examples described herein, the fusion pacing configuration may be referred to as "left-ventricular" pacing. However, it should be understood that a fusion pacing configuration may also include right-ventricular pacing in any of the examples described.

In some examples, when 1 MB 16 is in a biventricular pacing configuration, IMD 16 may deliver a pacing stimulus (e.g., a pacing pulse) to RV 28 via electrodes of lead 18 and a pacing stimulus to LV 32 via electrodes of lead 20 in a manner that synchronizes activation and contraction of RV 28 and LV 32.

As discussed in further detail below, IMD 16 may be configured to adjust one or more pacing parameters based on a cardiac status of heart 12. In some examples, IMD 16 may be configured to adjust a pacing parameter by delivering electrical stimulation therapy to heart 12 according to either a fusion pacing configuration or a biventricular pacing configuration.

In some examples, the CRT provided by 1 MB 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 26. The depolarization wave is transmitted through the atrial conduction pathways of Bachmann's Bundle and the Internodal Tracts at the atrial level into the LA 33 septum. When the atrial depolarization wave has reached the AV node, the atrial septum, and the furthest walls of the right and left atria 26, 33, respectively, the atria 26, 33 may contract as a result of the electrical activation. The aggregate right atrial and left atrial depolarization wave appears as the P-wave of the PQRST complex of an electrical cardiac signal, such as a cardiac electrogram (EGM) or electrocardiogram (ECG). When the amplitude of the atrial depolarization wave passing between a pair of unipolar or bipolar pace/sense electrodes located on or adjacent RA 26 and/or LA 33 exceeds a threshold, it is detected as a sensed P-wave. The sensed P-wave may also be referred to as an atrial sensing event, or an RA sensing event (RAs). Similarly, a P-wave sensed in the LA 33 may be referred to as an atrial sensing event or an LA sensing event (LAs).

During or after the atrial contractions, the AV node distributes the depolarization wave inferiorly down the Bundle of His in the intraventricular septum. The depolarization wave may travel to the apical region of heart 12 and then superiorly though the Purkinje Fiber network. The aggregate right ventricular and left ventricular depolarization wave and the subsequent T-wave accompanying repolarization of the depolarized myocardium may appear as the QRST portion of the PQRST cardiac cycle complex. When the amplitude of the QRS ventricular depolarization wave passing between a bipolar or unipolar pace/sense electrode pair located on or adjacent RV 28 and/or LV 32 exceeds a threshold, it is detected as a sensed R-wave. The sensed R-wave may also be referred to as a ventricular sensing event, an RV sensing event (RVs), or an LV sensing event (LVs) depending upon the ventricle in which the electrodes of one or more of leads 18, 20, 22 are configured to sense in a particular case.

Some patients, such as patients with congestive heart failure or cardiomyopathies, may have left ventricular dysfunction, whereby the normal electrical activation sequence through heart 12 is compromised within LV 32. In a patient with left ventricular dysfunction, the normal electrical activation sequence through the heart of the patient becomes disrupted. For example, patients may experience an intra-atrial conduction defect, such as intra-atrial block. Intra-atrial block is a condition in which the atrial activation is delayed because of conduction delays between RA 26 to LA 33.

As another example, a patient with left ventricular dysfunction may experience an interventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either RV 28 or LV 32 is delayed with respect to the other ventricle, causing asynchrony between the depolarization of the right and left ventricles. This asynchrony may result is decreased mechanical performance of the heart, which may be reflected in measures such as ejection fraction, stroke volume, LV pressure, and derivatives of LV pressure.

CRT delivered by IMD 16 may help alleviate heart failure conditions by restoring synchronous depolarization and contraction of one or more chambers of heart 12. In some cases, the fusion pacing of heart 12 described herein enhances mechanical performance of the heart of a patient by improving the synchrony with which RV 28 and LV 32 depolarize and contract. In some examples, measures of mechanical performance of the heart may be used to evaluate the efficacy of CRT and, in some cases, as feedback for modification of one or more parameters of CRT, such as A-V intervals or selections of which electrodes are used to deliver the CRT (or, as an alternative, an ICD shock treatment). However, measures of the mechanical performance of the left side of the heart tend to be invasive and thus disfavored for chronic monitoring of CRT efficacy. The techniques of this disclosure may allow system 10, e.g., IMD 16, to estimate such measures to determine efficacy of CRT and allow feedback control of CRT parameters.

In some examples, IMD 16 also provides defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical shocks. In some examples, IMD 16 is programmed to deliver a progression of therapies, e.g., shocks with increasing energy levels, until a fibrillation of heart 12 is stopped. In examples in which IMD 16 provides defibrillation therapy and/or cardioversion therapy, IMD 16 may detect fibrillation by employing any one or more fibrillation detection techniques known in the art.

External device 24 may be a computing device with a display viewable by a user and include an interface that receives input from a user. In some examples, external device 24 may be a notebook computer, tablet computer, workstation, one or more servers, cellular phone, personal digital assistant, or another computing device that may run an application that enables the computing device to interact with IMD 16. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, or other clinician, may interact with external device 24 to communicate with IMD 16. For example, the user may interact with external device 24 to retrieve physiological or diagnostic information from IMD 16. A user may also interact with external device 24 to program IMD 16, e.g., to select values for operational parameters of the IMD.

For example, the user may use external device 24 to retrieve information from IMD 16 regarding the rhythm of heart 12, trends therein over time, or arrhythmia episodes. As another example, the user may use external device 24 to retrieve information from IMD 16 regarding other sensed physiological parameters of patient 14, such as sensed electrical activity, activity, posture, respiration, thoracic impedance, or other data related to the techniques described herein from IMD 16. As another example, the user may use external device 24 to retrieve information from IMD 16 regarding the performance or integrity of IMD 16 or other components of system 10, such as leads 18, 20, and 22, or a power source of IMD 16. In such examples, physiological parameters of patient 14 and data regarding IMD 16 may be stored in a memory of IMD 16 for retrieval by the user.

The user may use external device 24 to program a therapy progression, select electrodes used to deliver defibrillation pulses, select waveforms for the defibrillation pulse, or select or configure a fibrillation detection algorithm for IMD 16. The user may also use external device 24 to program aspects of other therapies provided by IMD 16, such as cardioversion, CRT, or pacing therapies. In some examples, the user may activate certain features of IMD 16 by entering a single command via external device 24, such as depression of a single key or combination of keys of a keypad or a single point-and-select action with a pointing device.

Monitoring service 6, IMD 16, external device 24 and, optionally, another computing device (not illustrated in FIG. 1) may communicate via wireless communication using any techniques known in the art. External device 24, for example, may communicate via near-field communication technologies (e.g., inductive coupling, NFC or other communication technologies operable at ranges less than 10-20 cm) and far-field communication technologies (e.g., radiofrequency (RF) telemetry according to the 802.11 or Bluetooth® specification sets, or other communication technologies operable at ranges greater than near-field communication technologies). An example of a viable communication technique may include radiofrequency (RF) telemetry, for example, which may be an RF link established via an antenna according to Bluetooth, WiFi, or medical implant communication service (MICS), though other techniques are also contemplated. In some examples, external device 24 may include a programming head that may be placed proximate to the patient's body near the IMD 16 implant site in order to improve the quality or security of communication between IMD 16 and external device 24.

Processing circuitry of IMD 16, possibly in combination with processing circuitry of external device 24, may employ various techniques to capture physiological parameter signals over a period of time and then, analyze (e.g., parameter values encoded in) the captured physiological parameter signals for indicia of patient health including non-trivial changes in patient 14's cardiac health. The present disclosure describes IMD 16 as having access to a variety of hardware/software devices (e.g., as sensors coupled to IMD 16 and/or components of IMD 16) for generating the above signals, including electrodes, accelerometers, pressure sensors, force transducers, among other sensors. A number of physiological parameter signals transmit information indicative of patient 14's cardiac health and/or sensed cardiac activities, including electrical activity, pressure, movements/motion, and other environment features for bodily regions within and/or around heart 12. Examples of the above physiological parameter signals may include a cardiac EGM or ECG (i.e., cardiac EGM signals signals), heart motion data (e.g., accelerometer signals), pressure data (e.g., pressure sensor signals), and/or the like.

IMD 16 may be configured with logic to implement techniques to estimate values of one or more physiological parameters of patient 14 based on features of another, less-invasively acquired, physiological parameter. As described in the present disclosure, the logic may employ a number of compatible mechanisms to successfully implement the above technique, such as a mathematical or machine learning model (e.g., a neural network and/or a decision tree), where each mechanism prescribes criterion that the logic may use for estimating the physiological parameter values.

In some examples, the processing circuitry of medical system 10 analyzes patient data including data encoded in one or more physiological parameter signals (e.g., motion data of heart 12) representing patient cardiac activities sensed by IMD 16 and may identify indicia of a cardiac malady or abnormality, such as asynchrony. As described herein, directly sensing physiological parameters presents a number of difficulties for similar medical devices of IMD 16, such as having to configure a sensor (e.g., a pressure sensor) in (e.g., epicardial or endocardial) bodily positions (e.g., within a chamber of heart 12 such as a left ventricle). To illustrate by way of an example sensor for directly sensing pressure data for heart 12 of patient 14, FIG. 1 depicts pressure sensor 2 as being configured in an intrusive position likely to impede some cardiac function.

Processing circuitry of medical system 10, as described herein, enables indirect, and thus less invasive, sensing and monitoring of certain parameters of patient 14's cardiac health. For example, processing circuitry of medical system 10 generates a mechanism to support estimating left ventricle pressure data without directly sensing such data. IMD 16, as an example medical device such as the pacemaker described herein, employs an example machine learning technique that, in some instances, uses a trained model (e.g., a trained decision tree-based model) to compute estimates of left ventricle pressure data. Processing circuitry of IMD 16 may use these estimates to perform some functionality to patient 14's benefit (e.g., with respect to cardiac health) and, if applicable, replace direct pressure sensor measurements. In some instances, IMD 16 does to include any hardware/software components for directly sensing pressure within the left ventricle of patient 14's heart and instead, relies on the trained model for estimating sensed pressured data.

The present disclosure envisions medical devices that are equipped with a number of hardware/software components to implement different example techniques. Example medical devices (e.g., therapy devices including implants such as IMD 16) perform functionality to benefit of patient 14 and to operate effectively, facilitate that functionality with a number of configurable settings and direct sensing technologies to acquire physiological parameter data from body regions. Patient 14's body includes regions (e.g., organs such as the heart) that may be sensitive to any interaction and directly sensing (current) conditions (e.g., left ventricle pressure) in those regions may increase the likelihood of an adverse outcome for patient 14.

The example techniques may be used with an IMD 16, which may be in wireless communication with at least one of external device 24 and other devices not pictured in FIG. 1. In some examples, IMD 16 is implanted outside of a thoracic cavity of patient 14 (e.g., subcutaneously in the pectoral location illustrated in FIG. 1). IMD 16 includes a plurality of electrodes (not shown in FIG. 1), and is configured to sense a cardiac EGM via the plurality of electrodes, as well as a plurality of other sensors (not shown in FIG. 1) for sensing other physiological parameters, such as one or more accelerometers motion or vibration. Although described primarily in the context of examples in which IMD 16 is configured as a pacemaker configured to deliver CRT, the techniques described herein may be implemented in any implantable or external device to estimate one physiological parameter based on another. In some examples, IMD 16 takes the form of the LINQ™ ICM available from Medtronic, Inc. of Minneapolis, MN, an implantable or external defibrillator, an intracardiac pacemaker, a neurostimulator, or a drug pump.

Processing circuitry of medical system 10 facilitates training of the above decision tree-based model in an environment with considerably more resource capacities and capabilities than medical devices such as IMD 16. In one example, processing circuitry of a computing system of remote monitoring service 6 and/or processing circuitry of external device 24 execute another example machine learning technique, which may be referred to as a training process, to generate a distribution of pressure measurements from feature data. In general, the distribution represents the above-mentioned model and identifies mappings between feature data samples and estimates for left ventricle pressure, for example, in a multi-variate mathematical function or a decision tree, as some examples of the above-mentioned trained model. Prior to the training process, processing circuitry of medical system 10 may generate an untrained or pre-trained model and then, have the untrained or pre-trained model configured with no mappings (i.e., a null set) or populated with only default mappings. Using, as training data for the training process, the feature data samples and reference pressure measurements, processing circuitry of medical system 10 generates an initial set of mappings where the feature data samples are processed into an initial distribution (e.g., a linear distribution) of fitted reference pressure measurements. IMD 16 may be configured with a preclinically derived estimation algorithm to provide at the least the initial distribution and possibly, subsequent distributions for further training/calibration. The training process, according to some examples, may introduce a calibration step in which, over a number of iterations, processing circuitry of medical system 10 updates a previous model with a (more accurate) distribution of better fitting reference pressure measurements. In some examples, the training process incorporates into the calibration step patient-specific calibration in which patient-specific reference data (e.g., (non)-invasive pressure measurements, imaging data including echocardiographic data and electrocardiogram data, and/or the like) may be used to update the previous model and generate the trained model.

Medical system 10 includes a computing system communicatively coupled, over a network connection, to one or more medical devices including IMD 16 and, via wireless communication protocols, exchanges various data with IMD 16. Designated by medical system 10, the computing system may be configured to operate remote monitoring service 6 for IMD 16. Processing circuitry of medical system 10 may include one or more processors in the computing system of remote monitoring service 6 and, via communication circuitry, may receive from different devices of IMD 16, sensor signals storing sensed patient physiological parameters. At least some of these sensor signals are results from (directly) sensing those parameters from (intrusive or invasive) bodily positions (e.g., an epicardial position). The sensed physiological parameter (e.g., signals) include actual sensor measurements that may be employed as reference data for training machine learning models. In one example, remote monitoring service 6 may use the received patient physiological parameters as reference data for training an estimation model to accurately determine (e.g., predict) measurements and other values for one or more physiological parameters.

When the computing system of external device 24 and/or remote monitoring service 6 completes the above training process for an untrained decision tree-based model, external device 24 and/or monitoring service 6 deploys the trained decision tree-based model to IMD 16 to support that medical device's functionality by accurately computing pressure measurements and one or more derivatives for a volume within patient 14's left-ventricular heart chamber, for instance, while monitoring the patient's cardiac activity for an abnormal rhythm to detect and/or correct. Hence, the above decision tree-based model may be trained (offline) to leverage a resource-rich computing system and preserve valuable resources at IMD 16.

Remote monitoring service 6 and/or external device 24 may leverage a network communication with IMD 16 to receive, in a wireless communication, actual sensor measurements for training a machine learning model to operate as an accurate estimation model. In response to receiving the actual sensor measurements, remote monitoring service 6 and/or external device 24, in turn, may use the actual sensor measurements as reference data to update (e.g., further train) the deployed estimation model at IMD 16 to estimate future sensor measurements more accurately. In one example, pressure sensor 2 generates signals encoding actual pressure measurements and transmits, via the network communication, the generated signals to remote monitoring service 6 and/or external device 24. While IMD 16 may use the trained estimation model to determine estimated values of the same pressure measurements and then, use the estimated values in monitoring/correcting cardiac asynchrony, remote monitoring service 6 and/or external device 24 may push model updates to IMD 16.

Processing circuitry of medical system 10, in some examples, leverages the offline training for the above decision tree-based model to customize the above training process for patient 14 and/or IMD 16 and generate a personalize version of the above trained model. In this manner, a personalized decision tree-based model is configured to estimate left ventricle pressure specifically for patient 14's heart 12 or for any similar patient. The personalized decision tree-based model may be deployed to tailor IMD 16 to patient 14 (e.g., and some aspect of their physiology).

A number of other applications are conceivable in view of the present disclosure, including alternative/additional use cases for the systems, devices, and techniques described herein for determining future sensor measurements that are most likely to occur. According to one such use case, an estimation model may be configured for accurately predicting which values to expect from a given sensor in a device, while processing circuitry of medical system 10 may redirect the estimation model towards a different purpose, such as alternate prediction. The other applications are illustrative of the advantages of having the estimation model, such as the above decision tree-based model, in a medical device, such as IMD 16, of which one example use case is for enabling proactive alerts on behalf of patient 14.

Proactive alerts typically involve determining when human action (e.g., intervention) most likely will benefit patient 14 in some way (e.g., an improvement in patient health) and provide a number of benefits over reactive alerts and depending on patient 14's physiology (among other factors), may prevent sudden and/or critical health events from occurring. Some implementations enable the proactive alerts by applying the decision tree-based model to predict (with considerable accuracy) the future sensor measurements to expect at an upcoming point-in-time. and then, outputting a proactive alert based on the future sensor measurements; whereas, in other implementations, the decision tree-based model is integrated into a prediction model in which a number of factors determine when to output the proactive alert.

To demonstrate one or more benefits in an illustrative example, IMD 16 may incorporate the decision tree-based model into an analysis for determining whether future sensor measurements justify a proactive alert, such as by outputting an alarm intended to bring the future sensor measurements to a physician's attention, thereby prompting the physician to perform an action. For instance, the alarm may notify the physician of an urgent need to perform an action that IMD 16 is not configured to do. If patient 14 has a pacing device, some example actions for the physician to perform include increasing treatment/drug intake or calling another physician. It should be noted that other devices send proactive alerts for notifying patient 14's physician, particularly in an environment with considerably more resource capacities and capabilities than pacemakers and other embodiments of IMD 16. In one example, processing circuitry of a computing system of remote monitoring service 6 and/or processing circuitry of external device 24 output the alarm for the physician to receive via a local output device or a remote output device.

Figure 2:
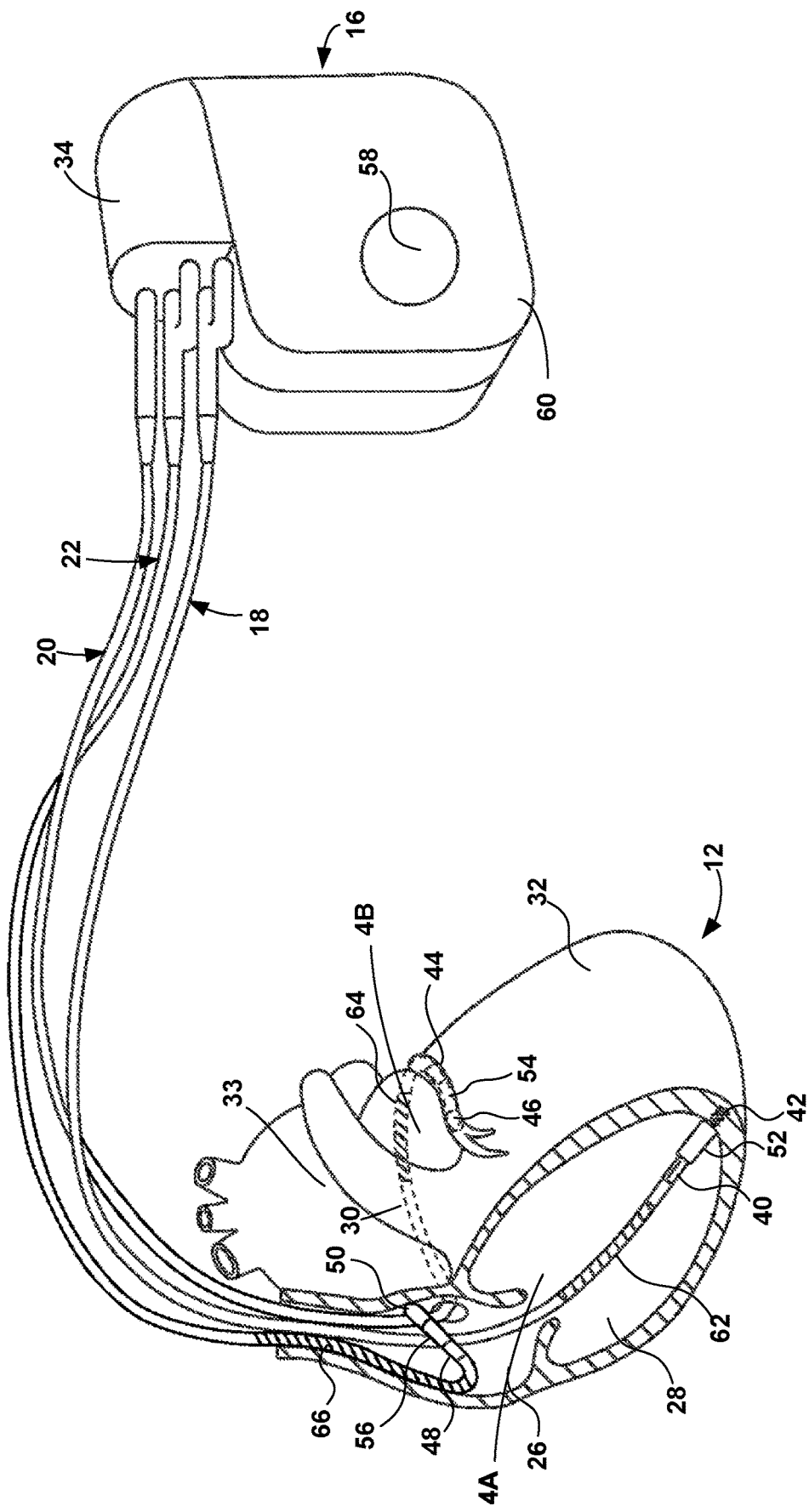
FIG. 2 is a conceptual diagram of an 1 MB in the example medical system of FIG. 1, in accordance with one or more examples of the present disclosure.

FIG. 2 is a conceptual diagram illustrating IMD 16 and leads 18, 20, 22 of medical device system 10 in greater detail. Leads 18, 20, 22 may be electrically coupled to therapy delivery circuitry, sensing circuitry, or other circuitry of IMD 16 via connector block 34. In some examples, proximal ends of leads 18, 20, 22 include electrical contacts that electrically couple to respective electrical contacts within connector block 34. In addition, in some examples, leads 18, 20, 22 are mechanically coupled to connector block 34 with the aid of set screws, connection pins or another suitable mechanical coupling mechanism.

Each of the leads 18, 20, 22 includes an elongated insulative lead body, which may carry a number of conductors separated from one another by tubular insulative sheaths. In the illustrated example, bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. Electrodes 40, 44, and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses to LV 32 via electrodes 44, 46 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. Any of the electrodes 40, 42, 44, 46, 48, and 50 may be used for unipolar sensing or stimulation delivery in combination with housing electrode 58. As described in further detail with reference to FIG. 3, housing 60 may enclose therapy delivery circuitry that generates cardiac pacing pulses and defibrillation or cardioversion shocks, as well as sensing circuitry for monitoring the patient's heart rhythm.

In some examples, leads 18, 20, 22 may also include elongated electrodes 62, 64, 66, respectively, which may take the form of a coil. IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of medical system 10 illustrated in FIGS. 1 and 2 is one example, and is not intended to be limiting. In other examples, a therapy system may include extravascular electrodes, such as subcutaneous electrodes, epicardial electrodes, and/or patch electrodes, instead of or in addition to the electrodes of transvenous leads 18, 20, 22 illustrated in FIG. 1. Further, IMD 16 need not be implanted within patient 14. In examples in which IMD 16 is not implanted in patient 14, IMD 16 may deliver defibrillation pulses, pacing pulses, and other therapies to heart 12 via percutaneous leads that extend through the skin of patient 14 to a variety of positions within or outside of heart 12.

Figure 3:
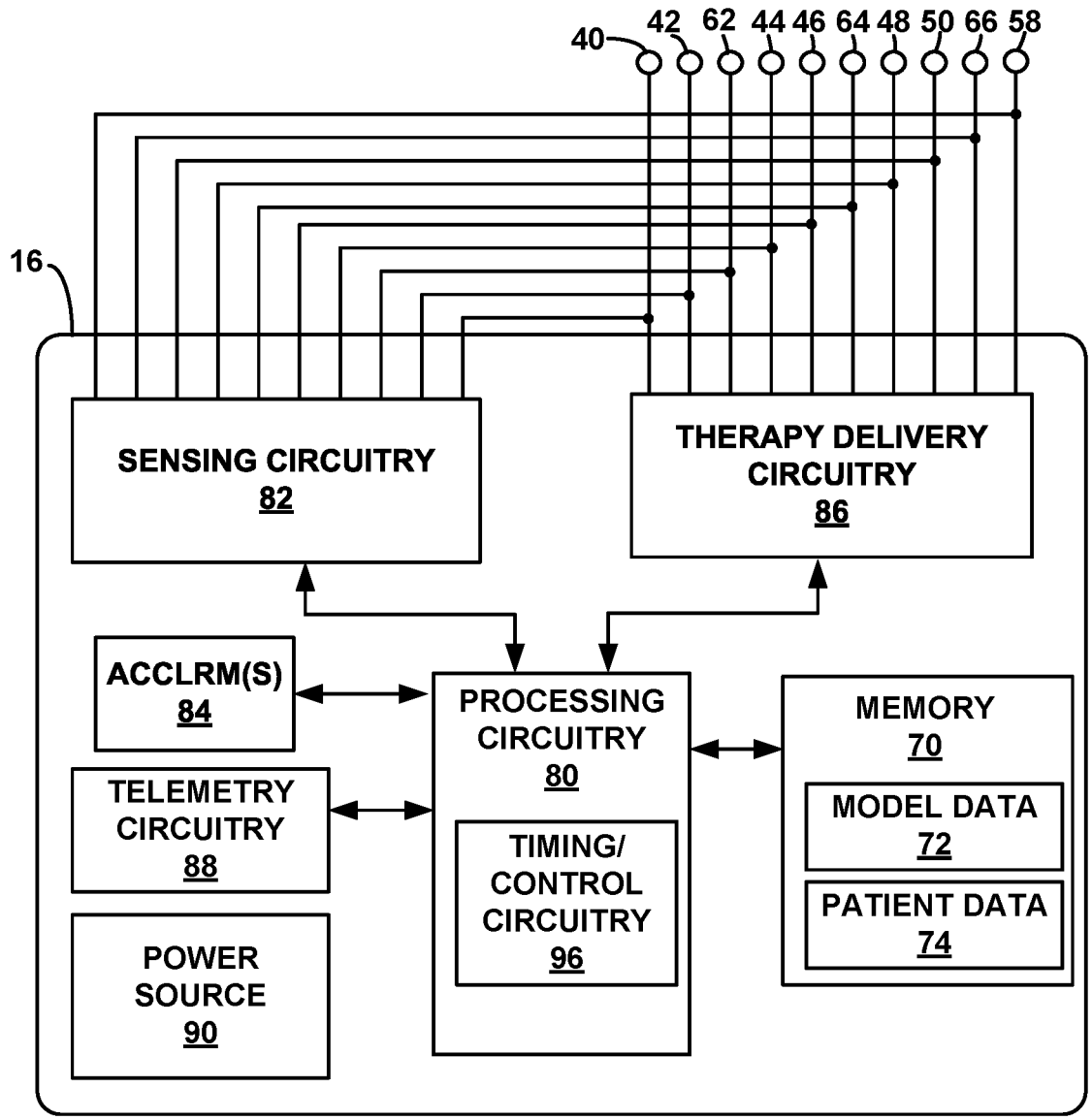
FIG. 3 is a block diagram illustrating an example configuration of the 1 MB of FIG. 2, in accordance with one or more examples of the present disclosure.

In other examples of medical device systems that provide electrical stimulation therapy to heart 12, a therapy system may include any suitable number of leads coupled to IMD 16, and each of the leads may extend to any location within or proximate to heart 12. For example, a therapy system may include a dual chamber device rather than a three-chamber device as shown in FIG. 1. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of RA 28 and LV 32.

In some examples, a medical device system includes one or more intracardiac pacing devices instead of, or in addition to, an IMD coupled to leads that extend to heart 12, like IMD 16. The intracardiac pacing devices may include therapy delivery and processing circuitry within a housing configured for implantation within one of the chambers of heart 12. In such systems, the plurality of pacing devices, which may include one or more intracardiac pacing devices and/or an IMD coupled to one or more leads, may communicate to coordinate sensing and pacing in various chambers of heart 12 to provide CRT according to the techniques described herein. Processing circuitry and memory of one or more of the pacing devices, and/or another implanted or external medical device, may provide the functionality for controlling delivery of CRT ascribed to processing circuitry and memory of IMD 16 herein.

As illustrated in FIG. 2, IMD 16 is communicatively coupled to one or more sensors that are positioned to sense aspects of a patient's cardiac health. A sensor may be configured in a location (e.g., near heart 12) for sensing cardiac activity, in particular, various physiological parameters corresponding to heart 12. Pressure sensor 2 is configured to generate signals (e.g., physiological parameter signals) to encode pressure data for heart 12 and to avoid negative effects of employing pressure sensor 2 for these signals, IMD16 uses a model to estimate the same pressure data; if the estimated pressure data satisfies a minimum accuracy requirement, IMD 16 may employ the estimated pressure data in detection logic for monitoring a cardiac abnormality and/or in therapy circuitry to correct the cardiac abnormality.

Although not illustrated in FIG. 2, system 10 may include one or more sensors, e.g., accelerometers or other mechanosensors, operative as intermediate or indirect sensors of pressure data (e.g., left ventricle pressure). As examples, a mechanosensor may be located at different locations, such as within IMD 16, at an endocardial or epicardial location of heart 12 (e.g., locations 4A and 4B, on the right and left ventricular free walls with proximity to the Mitral and Tricuspid valves), or on the left and/or right ventricular apices. The sensors may be disposed on one or more of leads 18, 20, 22, another lead not shown in FIG. 2, or may be wirelessly coupled to IMD 16. It should be noted that the sensors are not required to be within IMD 10 or on the heart, and, as an alternative, system 10 may employ at least one sensor of a body area network, which may be an in-body wireless cardiac sensor network.

Mechanosensors may each provide a first physiological parameter signal, such as an endocardial mechanosensory signal or an epicardial mechanosensory signal, encoding the first physiological parameter. System 10 may have the one or more sensors positioned in alternative locations other than within IMD 16 or the endocardial or epicardial locations mentioned herein; for example, the mechanosensor may be positioned in a vascular system of patient 14, such as a vascular compartment (e.g., transvenous) instead of at an end-tip of a cardiac lead (e.g. one or more of leads 18, 20, 22 or another lead not shown in FIG. 2). The mechanosensor may be configured as a stand-alone device when determining estimates of pulmonary or artery pressure within patient 14.

FIG. 3 is a block diagram illustrating an example configuration of IMD 16 of FIGS. 1 and 2. In the illustrated example, IMD 16 includes memory 70, processing circuitry 80, sensing circuitry 82, one or more accelerometers 84, therapy delivery circuitry 86, telemetry circuitry 88, and power source 90, one or more of which may be disposed within housing 60 of IMD 16.

In some examples, memory 70 includes computer-readable instructions that, when executed by processing circuitry 80, cause IMD 16 and processing circuitry 80 to perform various functions attributed to IMD 16 and processing circuitry 80 herein. Memory 70 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. In addition to sensed physiological parameters of patient 14 (e.g., EGM or ECG signals), one or more time intervals for timing fusion pacing therapy and biventricular pacing therapy to heart 12 may be stored by memory 70.

Figure 4:
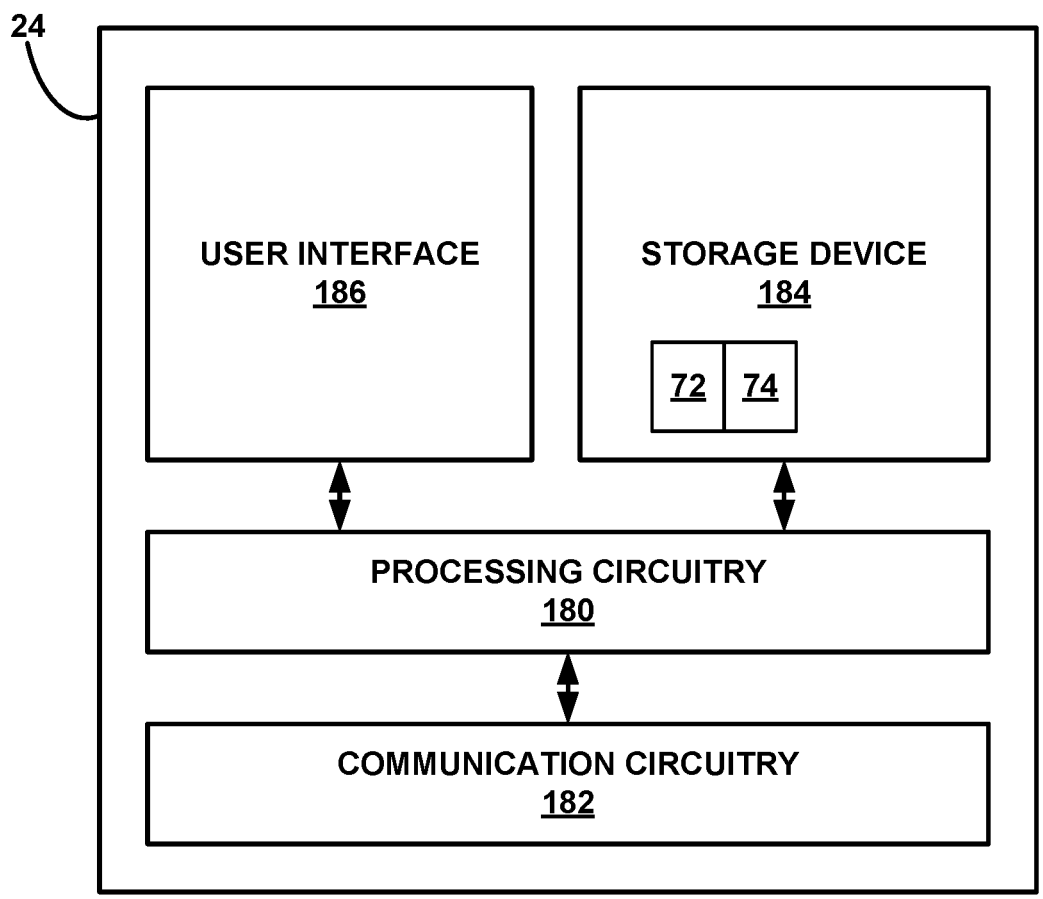
FIG. 4 is a block diagram illustrating an example configuration of the external device of FIG. 1, in accordance with one or more examples of the present disclosure.

In general, memory 70 may include various information datasets (e.g., database tables) and/or software components (e.g., software programs). As illustrated in the example of FIGS. 3 and 4, memory 70 may include model data 72 and patient data 74. In general, model data 72 refers to machine learning model (e.g., a decision tree model or a neural network) that is applied to patient data 74.

Processing circuitry 80 may include one or more of a microprocessor, a controller, digital signal processing circuitry (DSP), an application specific integrated circuit (ASIC), a field-programmable gate array (FPGA), or equivalent discrete or integrated logic circuitry. In some examples, processing circuitry 80 may include multiple components, such as any combination of one or more microprocessors, one or more controllers, one or more DSPs, one or more ASICs, or one or more FPGAs, as well as other discrete or integrated logic circuitry. The functions attributed to processing circuitry 80 herein may be embodied as software, firmware, hardware or any combination thereof. Processing circuitry 80 may be configured to determine a heart rate of heart 12 based on electrical activity sensed by sensing circuitry 82, estimate left ventricle pressure data (e.g., LV pressure and/or a derivative thereof) from leveraging machine learning resources of model data 72 of memory 70 and from various sensor data memorialized in patient data 74 (e.g., which may be codified into structured datasets of physiological parameters), and control the delivery CRT to heart 12 by therapy delivery circuitry 86 based on the left ventricular pressure data. With further respect to this example, processing circuitry 80 may be configured to cause therapy delivery circuitry 86 to deliver electrical pulses.

Sensing circuitry 82 is configured to monitor signals from at least one of electrodes 40, 42, 44, 46, 48, 50, 58, 62, 64 or 66 in order to monitor electrical activity of heart 12, e.g., via EGM signals. For example, sensing circuitry 82 may sense atrial events (e.g., a P-wave) with electrodes 48, 50, 66 within RA 26 or sense an LV 32 event (e.g., an R-wave) with electrodes 44, 46, 64 within LV 32. In some examples, sensing circuitry 82 includes switching circuitry to select which of the available electrodes are used to sense the electrical activity of heart 12. For example, processing circuitry 80 may select the electrodes that function as sense electrodes via the switching circuitry within sensing circuitry 82, e.g., by providing signals via a data/address bus. In some examples, sensing circuitry 82 includes one or more sensing channels, each of which may comprise an amplifier. In response to the signals from processing circuitry 80, the switching circuitry of sensing circuitry 82 may couple the outputs from the selected electrodes to one of the sensing channels.

In some examples, one channel of sensing circuitry 82 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing circuitry 82 may include a P-wave amplifier that receives signals from electrodes 48 and 50, which are used for pacing and sensing in RA 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing circuitry 82 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing circuitry 82 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 70 as an EGM. In some examples, the storage of such EGMs in memory 70 may be under the control of a direct memory access circuit. Processing circuitry 80 may employ digital signal analysis techniques to characterize the digitized signals stored in memory 70 to detect and classify the patient's heart rhythm from the electrical signals. Processing circuitry 80 may detect and classify the heart rhythm of patient 14 by employing any of the numerous signal processing methodologies known in the art.

Signals generated by sensing circuitry 82 may include, for example: an RA-event signal, which indicates a detection of a P-wave via electrodes implanted within RA 26 (FIG. 1); an LA-event signal, which indicates a detection of a P-wave via electrodes implanted within LA 33 (FIG. 1); an RV-event signal, which indicates a detection of an R-wave via electrodes implanted within RV 28; or an LV-event signal, which indicates a detection of an R-wave via electrodes implanted within LV 32. In the example of medical system 10 shown in FIGS. 1 and 2, IMD 16 is not connected to electrodes that are implanted within LA 33. However, in other example therapy systems, IMD 16 may be connected to electrodes that are implanted within LA 33 in order to sense electrical activity of LA 33.

In some examples, IMD 16 may include one or more additional sensors, such as accelerometers 84. In some examples, accelerometers 84 may comprise one or more three-axis accelerometers. As described above, accelerometers 84 may be an example of mechanosensors used to determine estimated LV pressure data according to the techniques described herein, and may be located within a housing of IMD 16, or coupled to IMD by one or more leads or a wireless connection. Signals generated by accelerometers 84 may be indicative of, for example, gross body movement of patient 14, such as a patient posture or activity level, as well as cardiac motion and vibration.

Therapy delivery circuitry 86 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of 1 MB 16. Therapy delivery circuitry 86 is configured to generate and deliver electrical stimulation therapy. For example, therapy delivery circuitry 86 may deliver a pacing stimulus to LV 32 (FIG. 2) of heart 12, in accordance with the fusion pacing techniques described herein, via at least two electrodes 44, 46 (FIG. 2). As another example, therapy delivery circuitry 86 may deliver a pacing stimulus to RV 28 via at least two electrodes 40, 42 (FIG. 2) and a pacing stimulus to LV 32 via at least two electrodes 44, 46 (FIG. 2), e.g., in accordance with the biventricular pacing techniques described herein.

In some examples, therapy delivery circuitry 86 is configured to deliver cardioversion or defibrillation shocks to heart 12. The pacing stimuli, cardioversion shocks, and defibrillation shocks may be in the form of stimulation pulses. In other examples, therapy delivery circuitry 86 may deliver one or more of these types of stimulation in the form of other signals, such as sine waves, square waves, or other substantially continuous time signals.

Therapy delivery circuitry 86 may include a switching circuitry, and processing circuitry 80 may use the switching circuitry to select, e.g., via a data/address bus, which of the available electrodes are used to deliver defibrillation pulses or pacing pulses. The switching circuitry may include a switch array, switch matrix, multiplexer, or any other type of switching device suitable to selectively couple stimulation energy to selected electrodes. In other examples, processing circuitry 80 may select a subset of electrodes 40, 42, 44, 46, 48, 50, 58, 62, 64, and 66 with which stimulation is delivered to heart 12 without a switching circuitry.

Processing circuitry 80 includes pacer timing and control circuitry 96, which may be embodied as hardware, firmware, software, or any combination thereof. Pacer timing and control circuitry 96 may comprise a dedicated hardware circuit, such as an ASIC, separate from other processing circuitry 80 components, such as a microprocessor, or a software module executed by a component of processing circuitry 80 (e.g., a microprocessor or ASIC). Pacer timing and control circuitry 96 may help control the delivery of pacing pulses to heart 12.

In examples in which 1 MB 16 delivers a pacing pulse, pacer timing and control circuitry 96 may include a timer for determining that a selected A-V interval has elapsed after processing circuitry 80 determines that an atrial pace or sense event ($A_{P/S}$, or more generally A) has occurred. The timer of pacing timing and control circuitry 96 may be configured to begin upon the detection of the preceding atrial pace or sense event ($A_{P/S}$) by processing circuitry 80. Upon expiration of the particular timer, processing circuitry 80 may control therapy delivery circuitry 86 to deliver a pacing stimulus, according to a fusion or biventricular pacing configuration, to heart 12. For example, pacing timing and control circuitry 96 may generate a trigger signal that triggers the output of a pacing pulse by therapy delivery circuitry 86.

In examples in which 1 MB 16 is configured to deliver other types of cardiac rhythm therapy in addition to fusion pacing and biventricular pacing, pacer timing and control circuitry 96 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to CRT, intervals defined by pacer timing and control circuitry 96 within processing circuitry 80 may include atrial and ventricular pacing escape intervals, refractory periods during which sensed P-waves and R-waves are ineffective to restart timing of the escape intervals, and the pulse widths of the pacing pulses. As another example, pacer timing and control circuitry 96 may define a blanking period, and provide signals from sensing circuitry 82 to blank one or more channels, e.g., amplifiers, for a period during and after delivery of electrical stimulation to heart 12. The durations of these intervals may be determined by processing circuitry 80 in response to stored data in memory 70. In some examples, the pacer timing and control circuitry 96 of processing circuitry 80 may also determine the amplitude of the cardiac pacing pulses.

During certain pacing modes, escape interval counters within pacer timing/control circuitry 96 of processing circuitry 80 may be reset upon sensing of R-waves and P-waves. Therapy delivery circuitry 86 may include pacer output circuits that are coupled, e.g., selectively by switching circuitry, to any combination of electrodes 40, 42, 44, 46, 48, 50, 58, 62, or 66 appropriate for delivery of a bipolar or unipolar pacing pulse to one of the chambers of heart 12. Processing circuitry 80 may reset the escape interval counters upon the generation of pacing pulses by therapy delivery circuitry 86, and thereby control the basic timing of cardiac pacing functions, including fusion cardiac resynchronization therapy.

The value of the count present in the escape interval counters when reset by sensed R-waves and P-waves may be used by processing circuitry 80 to measure the durations of R-R intervals, P-P intervals, P-R intervals and R-P intervals, which are measurements that may be stored in memory 70. Processing circuitry 80 may use the count in the interval counters to detect a tachyarrhythmia event, such as ventricular fibrillation event or ventricular tachycardia event. Upon detecting a threshold number of tachyarrhythmia events, processing circuitry 80 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processing circuitry 80 may operate as an interrupt driven device, and is responsive to interrupts from pacer timing and control circuitry 96, where the interrupts may correspond to the occurrences of sensed P-waves and R-waves and the generation of cardiac pacing pulses. Any necessary mathematical calculations to be performed by processing circuitry 80 and any updating of the values or intervals controlled by the pacer timing and control circuitry 96 of processing circuitry 80 may take place following such interrupts. A portion of memory 70 may be configured as a plurality of recirculating buffers, capable of holding series of measured intervals, which may be analyzed by processing circuitry 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processing circuitry 80 may utilize all or a subset of the rule-based detection methods described in U.S. Pat. No. 5,545,182 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,182 to Olson et al. and U.S. Pat. No. 5,755,736 to Gillberg et al. are incorporated herein by reference in their entireties. However, other arrhythmia detection methodologies may also be employed by processing circuitry 80 in other examples.

If IMD 16 is configured to generate and deliver defibrillation shocks to heart 12, therapy delivery circuitry 86 may include a high voltage charge circuit and a high voltage output circuit. In the event that processing circuitry 80 determines that generation of a cardioversion or defibrillation shock is required, processing circuitry 80 may employ the escape interval counter to control timing of such cardioversion and defibrillation shocks, as well as associated refractory periods. In response to the detection of atrial or ventricular fibrillation or tachyarrhythmia requiring a cardioversion pulse, processing circuitry 80 may activate a cardioversion/defibrillation control circuitry (not shown), which may, like pacer timing and control circuitry 96, be a hardware component of processing circuitry 80 and/or a firmware or software module executed by one or more hardware components of processing circuitry 80. The cardioversion/defibrillation control circuitry may initiate charging of the high voltage capacitors of the high voltage charge circuit of therapy delivery circuitry 86 under control of a high voltage charging control line.

Processing circuitry 80 may monitor the voltage on the high voltage capacitor, e.g., via a voltage charging and potential (VCAP) line. In response to the voltage on the high voltage capacitor reaching a predetermined value set by processing circuitry 80, processing circuitry 80 may generate a logic signal that terminates charging. Thereafter, timing of the delivery of the defibrillation or cardioversion pulse by therapy delivery circuitry 86 is controlled by a cardioversion/defibrillation control circuitry (not shown) of processing circuitry 80. Following delivery of the fibrillation or tachycardia therapy, processing circuitry 80 may return therapy delivery circuitry 86 to a cardiac pacing function and await the next successive interrupt due to pacing or the occurrence of a sensed atrial or ventricular depolarization.

Therapy delivery circuitry 86 may deliver cardioversion or defibrillation shock with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching circuitry of therapy delivery circuitry 86.

Telemetry circuitry 88 includes any suitable hardware, firmware, software or any combination thereof for communicating with another device, such as external device 24 (FIG. 1). Under the control of processing circuitry 80, telemetry circuitry 88 may receive downlink telemetry from and send uplink telemetry to external device 24 with the aid of an antenna, which may be internal and/or external. Processing circuitry 80 may provide the data to be uplinked to external device 24 and the control signals for the telemetry circuit within telemetry circuitry 88, e.g., via an address/data bus. In some examples, telemetry circuitry 88 may provide received data to processing circuitry 80 via a multiplexer.

In some examples, processing circuitry 80 may transmit atrial and ventricular heart signals (e.g., EGM signals) produced by atrial and ventricular sense amp circuits within sensing circuitry 82 to external device 24. Other types of information may also be transmitted to external device 24, such as the various intervals and delays used to deliver CRT. External device 24 may interrogate IMD 16 to receive the heart signals. Processing circuitry 80 may store heart signals within memory 70, and retrieve stored heart signals from memory 70. Processing circuitry 80 may also generate and store marker codes indicative of different cardiac episodes that sensing circuitry 82 detects, and transmit the marker codes to external device 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis. IMD 16 may leverage a remote computing device such as external device 24 and/or remote monitoring service 6 for additional resources (e.g., processing power), for example, to execute a training process for generating a trained version of the machine learning model for implementing the parameter estimation techniques described herein.

Medical system 10 may be a computing system running in a single device or over a network of devices. IMD 16, a medical device, is one example device but other device types may be included. IMD 16 includes a mechanosensor configured to sense a first physiological parameter signal of a patient; and processing circuitry 80 configured to: determine one or more features of the first physiological parameter signal; apply a machine leaning model to the one or more features of the first physiological parameter signal; and based on the application of the machine learning model, determine an estimated value of a second physiological parameter.

In one example, medical system 10 may configure the mechanosensor to sense a first physiological parameter signal including one or both of an endocardial mechanosensory signal or an epicardial mechanosensory signal encoding data for the first physiological parameter (e.g., accelerometer data). As an alternative, medical system 10 may configure the mechanosensor to sense a transvenous mechanosensory signal as the first physiological parameter signal. Within IMD 16, the mechanosensor may be configured to sense the first physiological parameter signal in either endocardial, epicardial, or thoracic bodily positions of the patient.

One example of the second physiological parameter, pressure, may be estimated in accordance with the machine learning model of model data 72. It should be noted that other parameters may be estimated using the same or similar techniques. In one example, medical system 10 may include processing circuitry, such as processing circuitry 80 of IMD 16, to determine an estimated value of a parameter corresponding to pressure with a chamber of the patient's heart, such as a left-ventricular pressure measurement. Model data 72 may include a readable and structured representation of the machine learning model such that processing circuitry 80 may execute instructions for an application of the model to one or more extracted features from first physiological parameters signals. Based on that application, for example, processing circuitry 80 is configured to generate an estimate of the left-ventricular pressure measurement based on an endocardial or epicardial mechanosensory signal.

After (or instead of) determining one or more estimated values of the second physiological parameter, such as left-ventricular pressure measurements, processing circuitry 80 is further configured to compute one or more derivatives of a particular left-ventricular pressure measurement. If the particular left-ventricular pressure measurement is based on an application of the above machine learning model on an endocardial or epicardial mechanosensory signal, the one or more derivatives also are based on the endocardial or epicardial mechanosensory signal. Estimates of left-ventricular pressure measurements and any derivative values are based on one or more features extracted from the endocardial or epicardial mechanosensory signal.

In general, applying the machine learning model involves extracting one or more features from the first physiological parameter signal and then, executing one or more (e.g., mathematical) functions using the one or more features as input data. In one example, processing circuitry 80 extracts data for the one or more features from the endocardial or epicardial mechanosensory signal, or another example first physiological parameters signal. Based on the application of the machine learning model by processing circuitry 80 to such feature data, processing circuitry 80 is configured to determine an estimated value of the second physiological parameter (signal), such as the above-mentioned pressure data. In one example, processing circuitry 80 is configured to compute example pressure data including an estimate of a pressure measurement in a specific heart chamber of the patient. To calibrate therapeutic responses to cardiac asynchrony, processing circuitry 80 may compute the estimated pressure measurement for the left ventricle chamber. It should be noted that pressure data for another chamber may also be estimated and then, those estimates may be used in directing the patient's therapy.

In one example, the machine leaning model is applied to one or more features corresponding to a first physiological parameter encoded in the endocardial or epicardial mechanosensory signal. Accelerometer data may describe movements in the patient's heart and, as an example parameter, may be encoded in endocardial or epicardial mechanosensory signals; those movements may be further processed into an estimate of a second physiological parameter, such as (e.g., a current or contemporaneous) pressure measurement for a chamber in the patient's heart.

IMD 16 of medical system 10 may configure processing circuitry 80 to use the estimated value of the second physiological parameter in a variety of applications, including monitoring/detection, therapy, and other functionality. In an example evaluation of patient data, the estimated value of a (current) left ventricle pressure measurement may be used in determined whether the patient's cardiac activity has cardiac synchrony. The medical system may rely on such an evaluation to determine whether to provide therapy to correct an abnormal cardiac rhythm. Processing circuitry 80 may execute logic configured to identify cardiac activity indicative of an abnormal cardiac rhythm. Based on one or more estimated pressure measurements for the patient's left ventricle, processing circuitry 80 may detect the instance of the abnormal cardiac rhythm. Processing circuitry 80 may be configured to apply a therapeutic response to the identified cardiac activity indicative of the abnormal cardiac rhythm and that therapeutic response may be based on the estimated left ventricle pressure measurements, as the example second physiological parameter.

To further reduce false positives or false negatives, processing circuitry 80 may perform update the machine learning model to achieve a higher accuracy level. Such an updated may be based on a comparison between the estimated values of the second physiological parameter, such as the above left ventricle pressure measurements, and a reference value corresponding to the same or similar parameter. To illustrate an example iteration of the training process executed by the above computing system, processing circuitry of medical system 10, in response to receiving estimated left ventricle pressure measurements from the medical device, updates the machine learning model by comparing the estimated left ventricle pressure measurements for a heart of the patient to reference pressure data and adjusting a component of the machine learning model based on the comparison.

To train an initial version of the machine learning model until at least a minimal level of accuracy, medical system 10 may include a computing system for running a training process on the model's components. In general, the training process evaluates a given machine learning model with respect to accuracy (e.g., an accuracy metric) by comparing estimated values of the second physiological parameter with actual (e.g., sensed or measured) parameter values and based on a comparison, adjusting one or more model components (e.g., weights, thresholds, and/or the like) such that the adjusted machine learning model is configured to produce modified estimated values that are more accurate than the previous estimated values. The machine learning model may be adjusted to reduce a difference (e.g., residual) between an estimated value and a corresponding reference value for the same parameter. Processing circuitry of medical system 10 may executing the training process on a corpus of cardiac activity data for a patient population or a patient sub-group and for a number of iterations, adjusts the machine learning model to increase the accuracy of each estimation. Ultimately, the processing circuitry of medical system 10 generates a trained version of the machine learning model.

The above computing system (e.g., cloud computing environment) for medical system 10 may be communicatively coupled, over a network (e.g., a wireless network), to a plurality of medical devices including IMD 16. After executing the training process on some training data (e.g., the corpus of cardiac activity data for a patient population or a patient sub-group) and generating the trained version of the machine learning model to accurately determine an estimated value of a left ventricle pressure measurement (or another example second physiological parameter), processing circuitry of the above computing system may be configured to deploy the (trained) machine learning model for implementation in IMD 16 or another medical device configured to monitor the patient's cardiac activity and, if possible, provide a therapeutic response.

Examples of mechanosensors to sense patient activity include an accelerometer (e.g., a three-axis accelerometer), a gyroscope, a temperature gauge, a moment transducer, and/or the like. There are a number of methods for converting the encoded patient activity into one or more physiological parameters, each of which may be a quality (e.g., high activity, low activity, and/or the like) or a quantity (e.g., a number of activity minutes or fractional activity minutes (e.g., 10-second blocks)), representing some aspect of the patient's physiology. Various metrics (e.g., accuracy metrics) levels enable standardized measurement of each sample (e.g., timestamp) of physiological parameter data and differentiation between multiple samples (e.g., timestamps or longer time periods and/or patients) of physiological parameter data.

In some examples, processing circuitry 80 executes the detection logic to monitor for abnormalities in cardiac rhythm and/or maladies known as cardiac events, including arrhythmias, that are likely to cause a decline in patient health or, otherwise, negatively affect the patient's heart. The detection logic may be configured to determine whether the cardiac EGM data or ECG data is indicative of such cardiac episodes, for instances, based on one or more criterion. As described herein, processing circuitry 80 may rely on alternative data sources for information describing an aspect of patient 14's cardiac activity. As a substitute for a certain sensor and its measurements, processing circuitry 80 may avail a model (e.g., a machine learning model) to estimate such measurements and then, replace that sensor data in the detection analysis. The sensor data may be generated by one or more sensors of sensors 62 directly sensing that data from within patient 14's body, in particular, patient 14's heart.

In some examples, processing circuitry 80 incorporates a decision-tree model into the detection logic and then, applies the decision-tree model to estimate left ventricle pressure data from input feature data as an improvement to using a pressure sensor to directly sense left ventricle pressure from that heart chamber. In some examples, processing circuitry 80 may use the decision-tree model to compute derivatives of the left ventricle pressure data. Instead of a conventional sensor device (e.g., a pressure sensor) directly sensing left ventricle pressure and its derivatives, processing circuitry 80 leverages an endo or epicardial mechanosensory signal (e.g., accelerometer) for patient activity data to use in computing an estimate of left ventricle pressure (e.g., at a same timestamp). There are number of mechanisms for measuring patient activity at a specific time, such as the 10sec23count method, which checks whether integrated counts of a frontal (z-axis) accelerometer reach a 23-count threshold within each of consecutive 10-second windows. Processing circuitry 80 of IMD 16 may apply the 10sec23count method to the integrated counts over a pre-determined time period (e.g., a minute or hour).

FIG. 4 is a block diagram illustrating an example configuration of components of external device 24. In the example of FIG. 4, external device 24 includes processing circuitry 180, communication circuitry 182, storage device 184, and user interface 186.

Processing circuitry 180 may include one or more processors that are configured to implement functionality and/or process instructions for execution within external device 24. For example, processing circuitry 180 may be capable of processing instructions stored in storage device 184. Processing circuitry 180 may include, for example, microprocessors, DSPs, ASICs, FPGAs, or equivalent discrete or integrated logic circuitry, or a combination of any of the foregoing devices or circuitry. Accordingly, processing circuitry 180 may include any suitable structure, whether in hardware, software, firmware, or any combination thereof, to perform the functions ascribed herein to processing circuitry 180.

Communication circuitry 182 may include any suitable hardware, firmware, software or any combination thereof for communicating with another device, such as IMD 16. Under the control of processing circuitry 180, communication circuitry 182 may receive downlink telemetry from, as well as send uplink telemetry to, IMD 16, or another device. Communication circuitry 182 may be configured to transmit or receive signals via inductive coupling, electromagnetic coupling, NFC, RF communication, Bluetooth, WiFi, or other proprietary or non-proprietary wireless communication schemes. Communication circuitry 182 may also be configured to communicate with devices other than IMD 16 via any of a variety of forms of wired and/or wireless communication and/or network protocols.

Storage device 184 may be configured to store information within external device 24 during operation. Storage device 184 may include a computer-readable storage medium or computer-readable storage device. In some examples, storage device 184 includes one or more of a short-term memory or a long-term memory. Storage device 184 may include, for example, RAM, DRAM, SRAM, magnetic discs, optical discs, flash memories, or forms of EPROM or EEPROM. In some examples, storage device 184 is used to store data indicative of instructions for execution by processing circuitry 180. Storage device 184 may be used by software or applications running on external device 24 to temporarily store information during program execution.

Data exchanged between external device 24 and IMD 16 may include operational parameters. External device 24 may transmit data including computer readable instructions which, when implemented by IMD 16, may control IMD 16 to change one or more operational parameters and/or export collected data. For example, processing circuitry 180 may transmit an instruction to IMD 16 which requests IMD 16 to export collected data (e.g., asystole episode data) to external device 24. In turn, external device 24 may receive the collected data from IMD 16 and store the collected data in storage device 184, for example, as a portion of model data 72 and/or patient data 74. The data external device 24 receives from IMD 16 may include patient data 74, and similar to FIG. 3, patient data 74 includes patient physiological parameter data, episode data (e.g., cardiac EGMs), patient activity and other sensor data. Processing circuitry 180 may implement any of the techniques described herein to use model data 72 as an estimation model for predicting values for current or future sensor measurements. As described, examples of the sensor measurements may correspond to sensed patient cardiac activities. Similar to processing circuitry 80 of IMD 16, processing circuitry 180 may use the estimation model to analyze patient data 74 from IMD 16 and determine estimated values of pressure sensor 2 measurements at one or more points-in-time e.g., to determine whether patient 14 is experiencing a change in health e.g., based upon one or more criteria.

A user, such as a clinician or patient 14, may interact with external device 24 through user interface 186. User interface 186 includes a display (not shown), such as a liquid crystal display (LCD) or a light emitting diode (LED) display or other type of screen, with which processing circuitry 180 may present information related to IMD 16, e.g., patient data 74 as described herein. In addition, user interface 186 may include an input mechanism configured to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 180 of external device 24 and provide input. In other examples, user interface 186 also includes audio circuitry for providing audible notifications, instructions or other sounds to the user, receiving voice commands from the user, or both.

Figure 5:
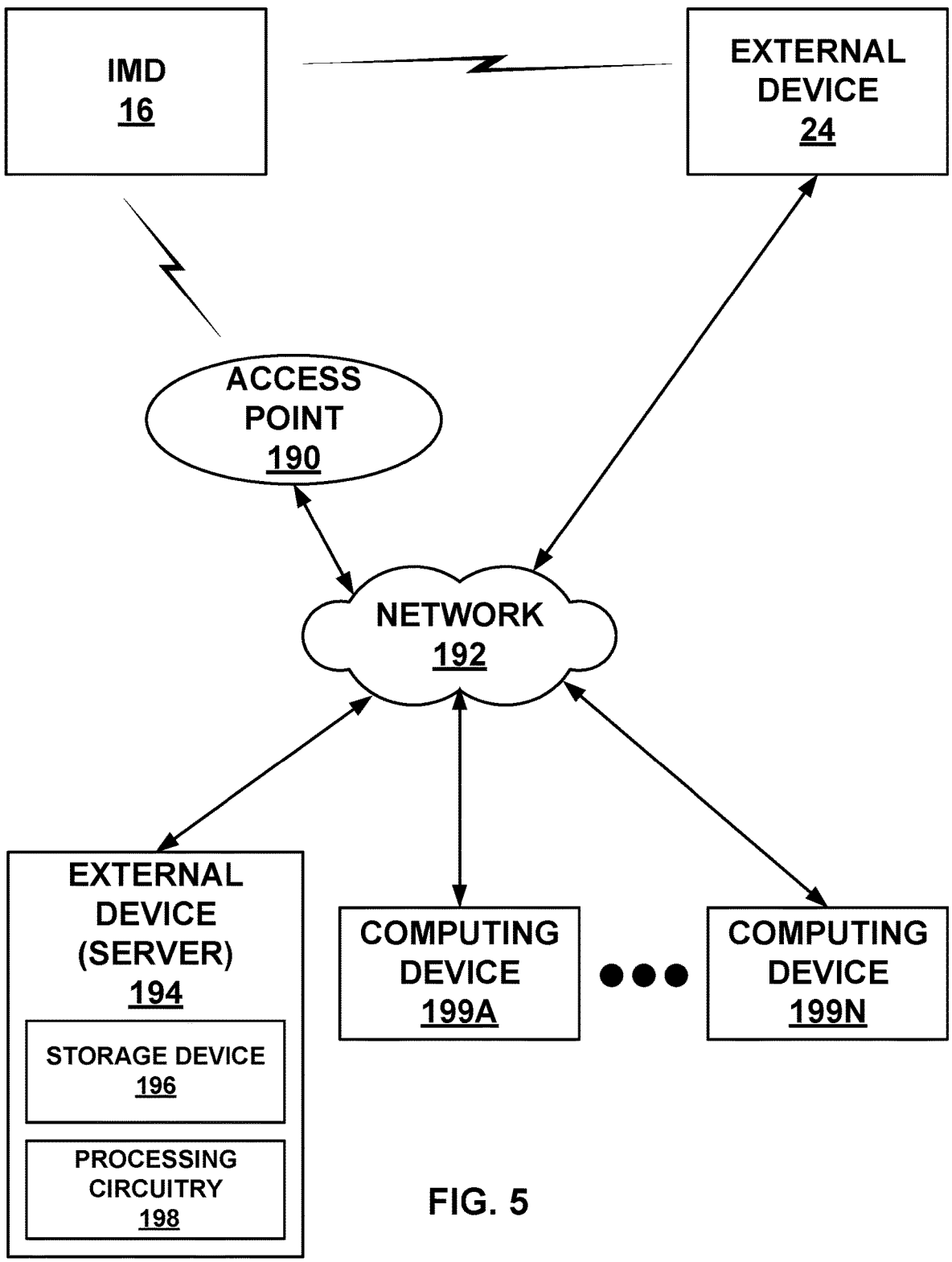
FIG. 5 is a block diagram illustrating an example system that includes an access point, a network, external computing devices, such as a server, and one or more other computing devices, which may be coupled to the medical device and external device of FIGS. 1-4, in accordance with one or more examples of the present disclosure.

FIG. 5 is a block diagram illustrating an example system that includes an access point 190, a network 192, external computing devices, such as a server 194, and one or more other computing devices 199A-199N (collectively, "computing devices 199"), which may be coupled to IMD 16 and external device 24 via network 192, in accordance with one or more techniques described herein. In this example, IMD 16 may use communication circuitry 154 to communicate with external device 24 via a first wireless connection, and to communicate with an access point 190 via a second wireless connection. In the example of FIG. 5, access point 190, external device 24, server 194, and computing devices 199 are interconnected and may communicate with each other through network 192.

Access point 190 may include a device that connects to network 192 via any of a variety of connections, such as telephone dial-up, digital subscriber line (DSL), or cable modem connections. In other examples, access point 190 may be coupled to network 192 through different forms of connections, including wired or wireless connections. In some examples, access point 190 may be a user device, such as a tablet or smartphone, that may be co-located with the patient. IMD 16 may be configured to transmit data, such as patient data 74 that describes patient 14's cardiac activity over a pre-determined time period, and/or indications of changes in patient health, to access point 190. Access point 190 may then communicate the retrieved data to server 194 via network 192.

As described herein, medical devices other than IMD 16 may generate data by directly sensing patient cardiac activity from a position within the patient's body, particular, within the patient's heart. IMD 16 and similar medical devices, in contrast, forgo direct sensing and implement a machine learning model and technique for estimating left ventricle pressure, as a replacement for data generated by direct sensing. While the estimated left ventricle pressure data may rely on feature data from one or more sensors, IMD 16 does not utilize a typical or conventional sensor for directly sensing left ventricle pressure. Any sensor data used in the estimation is generated from non-invasive and/or passive means.

In some cases, server 194 may be configured to provide a secure storage site for data that has been collected from IMD 16 and/or external device 24. In some cases, server 194 may assemble data in web pages or other documents for viewing by trained professionals, such as clinicians, via computing devices 199. One or more aspects of the illustrated system of FIG. 5 may be implemented with general network technology and functionality, which may be similar to that provided by the Medtronic CareLink® Network.

In some examples, one or more of computing devices 199 may be a tablet or other smart device located with a clinician, by which the clinician may program, receive alerts from, and/or interrogate IMD 16. For example, the clinician may access patient data including estimated left ventricle pressure measurements and/or indications of patient health collected by IMD 16 through a computing device 199, such as when patient 14 is in in between clinician visits, to check on a status of a medical condition. In some examples, the clinician may enter instructions for a medical intervention for patient 14 into an application executed by computing device 199, such as based on a status of a patient condition determined by IMD 16, external device 24, server 194, or any combination thereof, or based on other patient data known to the clinician. Device 199 then may transmit the instructions for medical intervention to another of computing devices 199 located with patient 14 or a caregiver of patient 14. For example, such instructions for medical intervention may include an instruction to change a drug dosage, timing, or selection, to schedule a visit with the clinician, or to seek medical attention. In further examples, a computing device 199 may generate an alert to patient 14 based on a status of a medical condition of patient 14, which may enable patient 14 proactively to seek medical attention prior to receiving instructions for a medical intervention. In this manner, patient 14 may be empowered to take action, as needed, to address his or her medical status, which may help improve clinical outcomes for patient 14.

In the example illustrated by FIG. 5, server 194 includes a storage device 196, e.g., to store data retrieved from IMD 16, and processing circuitry 198. Although not illustrated in FIG. 5 computing devices 199 may similarly include a storage device and processing circuitry. Processing circuitry 198 may include one or more processors that are configured to implement functionality and/or process instructions for execution within server 194. For example, processing circuitry 198 may be capable of processing instructions stored in storage device 196. Processing circuitry 198 may include, for example, microprocessors, DSPs, ASICs, FPGAs, or equivalent discrete or integrated logic circuitry, or a combination of any of the foregoing devices or circuitry. Accordingly, processing circuitry 198 may include any suitable structure, whether in hardware, software, firmware, or any combination thereof, to perform the functions ascribed herein to processing circuitry 198. Processing circuitry 198 of server 194 and/or the processing circuitry of computing devices 199 may implement any of the techniques described herein to analyze various information in the patient received from IMD 16, e.g., to (further) evaluate the left ventricle pressure estimates determined by a model at IMD 16, (further) train the model used by IMD 16 to determine the left ventricle pressure estimates, to (further) perform functionality in support of a remote monitoring service, and determine whether the health status of a patient has changed.

Storage device 196 may include a computer-readable storage medium or computer-readable storage device. In some examples, storage device 196 includes one or more of a short-term memory or a long-term memory. Storage device 196 may include, for example, RAM, DRAM, SRAM, magnetic discs, optical discs, flash memories, or forms of EPROM or EEPROM. In some examples, storage device 196 is used to store data indicative of instructions for execution by processing circuitry 198.

Figure 6A:
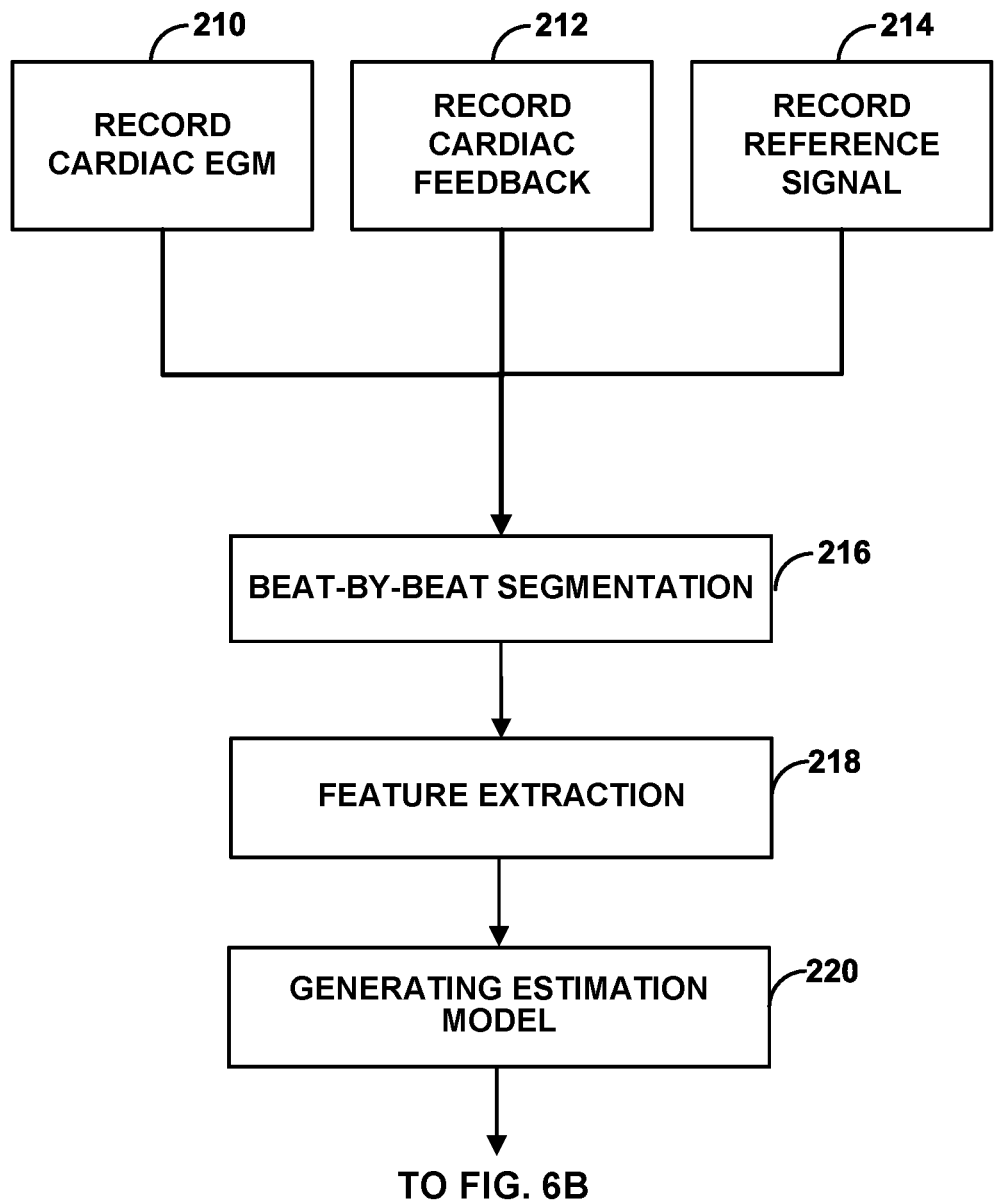
FIG. 6A is a flow diagram illustrating a first stage of a machine learning technique to enable less invasive monitoring of a physiological parameter, in accordance with one or more examples of the present disclosure.
Figure 6B:
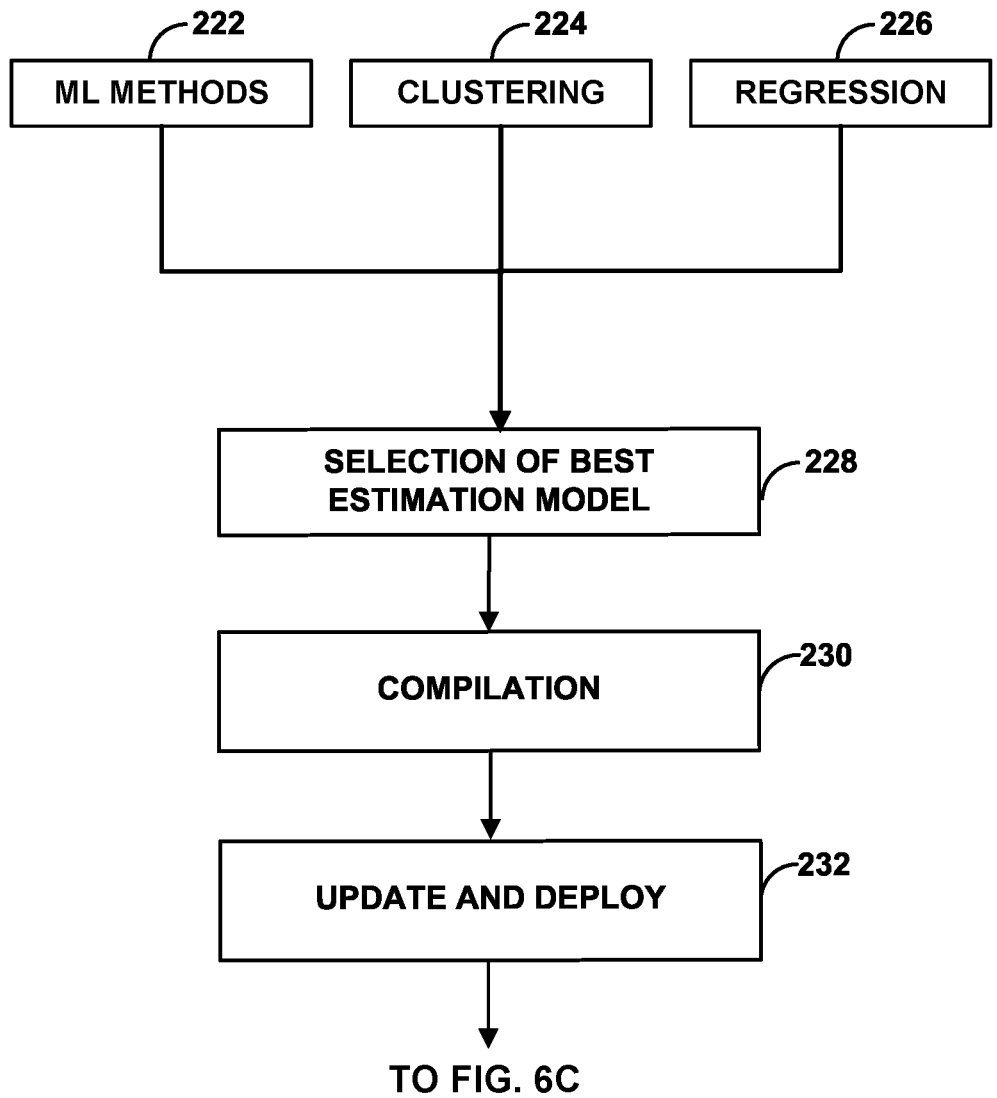
FIG. 6B and FIG. 6C are flow diagrams illustrating a second stage and a third stage, respectively, of the machine learning technique of FIG. 6A, in accordance with one or more examples of the present disclosure.
Figure 6C:
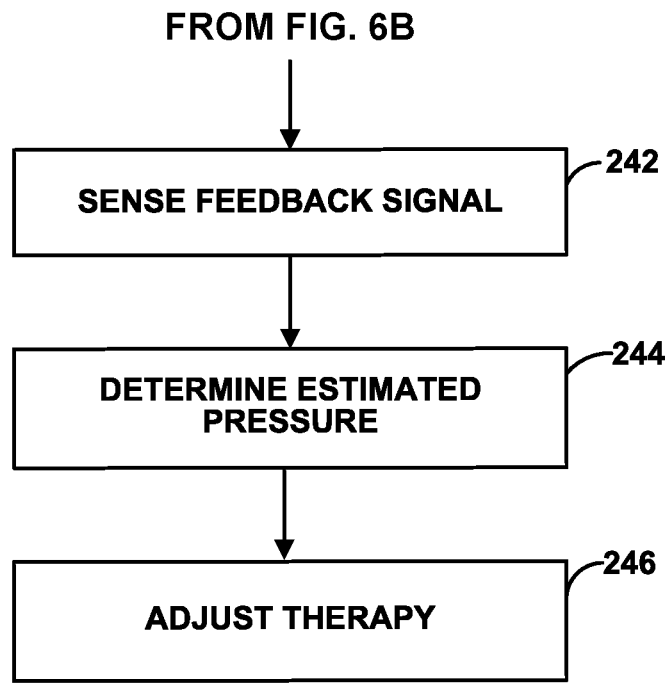

The following description relates to flow diagrams FIGS. 6A-6C and FIGS. 7A-7C, which respectively illustrate examples of a first machine learning technique and a second machine learning technique. As described herein, the first machine learning technique enables non-invasive care from a medical device. FIGS. 6A-6C further describe the first machine learning technique as a pipeline (e.g., an automated processing pipeline) for chronic tracking of cardiac function via mechanism feedback classification using machine learning. When implemented in medical devices (e.g., implanted cardiac monitor devices), the pipeline enables additional functionality in support of cardiac monitoring applications. The patient further benefits, in some examples, with non-invasive care from the medical device.

FIG. 6A is a flow diagram illustrating a first stage of the first machine learning technique, in accordance with one or more examples of the present disclosure.

The first stage, in general, includes a training process for a machine learning model. In FIG. 6A, the first stage is visualized as a process flow that results in an initial estimation model to effectuate the additional functionality of the medical device. Each additional function benefits the patient and the medical device in at least one respect as described herein. Given the availability of training datasets and ubiquitous nature of machine learning training, the present disclosure envisions a wide variety for the additional functionality; as one example of an added function to normal device operation, the medical device may use the estimation model to estimate left ventricle pressure data as a substitute for directly sensing the pressure in the left ventricle chamber of the patient's heart. While estimating left ventricle pressure data is one example, a substantial number of additional functions are foreseeable from the present disclosure.

FIG. 6A illustrates the training process of the above machine learning model to enable accurate estimation of the left ventricle pressure measurements. It should be noted that other additional functions envisioned by the present disclosure may be generated via the first machine learning technique. In accordance with the first machine learning technique, the training process utilizes recorded data consisting of representations (e.g., cardiac EGMs) of patient cardiac activity (210), cardiac feedback (e.g., mechanical feedback) from medical device components in endocardial, epicardial, and/or thoracic bodily positions (212), and reference signals (e.g., estimation signals) encoding actual measurements from one or more sensors (e.g., pressure sensor 2 of FIG. 1 and FIG. 2).

In some examples of the first machine learning technique, the training process performs a beat-by-beat segmentation of the record data (216) where for each heart beat, at least one actual sensor measurement (e.g., corresponding to heart 12) is compared with at least one corresponding estimate generated by a machine learning model (i.e., an estimation model) and based on that comparison, an adjustment is made to at least one model component (e.g., a parameter weight) to improve upon the model's accuracy. For a first iteration of the training process, the machine learning model may be untrained or insufficiently trained for estimating values of the patient's physiological parameters. Over a number of iterations, the machine learning model may be fully trained and therefore, suitable for monitoring a patient's cardiac health for abnormalities (e.g., cardiac asynchrony) and, if possible, providing a therapeutic response to correct/treat the abnormalities.

The training process determines which adjustment to make based on whether the resulting model generates a more accurate estimate of the at least one corresponding estimate. Processing circuitry as described herein may use the machine learning model to predict a sensor measurement (e.g., a pressure measurement of a left ventricle) by computing an estimated value from a computational algorithm or a mathematical function. The computational algorithm or mathematical function may include input variables corresponding to various feature values. The processing circuitry may execute software code to perform feature extraction on training datasets (218) and determine the various feature values for the computational algorithm or a mathematical function. Based on a difference between the estimated value and a corresponding actual sensor measurement (e.g., of the recorded reference data), the model is adjusted by modifying the computational algorithm or mathematical function to reduce the difference value. As a result, the adjusted model may be used to compute a new estimated value that is closer to the corresponding actual sensor measurement.

After a number of adjustments, the training process may generate an initial estimation model for eventual deployment to medical devices (220). In one example, the training process employs a corpus of cardiac activity data for a patient population and generates the initial estimation model to be a generic model that is applicable to most (if not all) patients. In other examples, the training process employs cardiac activity data for a patient sub-group or a specific patient (e.g., patient 14 of FIG. 1) and generates the initial estimation model to be a personalized model.

To establish personalized models offline according to the first machine learning technique, an external computing device performs the training process and partitions the training data into patient groups and/or individual patients. Patients can be grouped in a number of ways, in one example, by patient demographics). The training process coordinates the training of each personalized model amongst primarily using training data for similar patients in a specific group and/or specific patient.

As described herein, an autonomous analysis is performed in the signals wherein beats are segmented and predetermined features are extracted on a beat by beat basis. The initial recording allows personalization of the models to the respective patient that will receive the device. External data sources may be used instead of the patient recordings directly, in order to train a more generalized and robust model. A combination of these two methods may be used as a number of machine learning applications, for which a personalized model can be appended to a previously generated general model.

Once trained, these personalized models can estimate cardiac function pressure or selected measures on a beat by beat basis for identification of CRT non-responders and heart failure regression by using the implanted mechanosensor for intermediate measurement data. This eliminates the need for direct sensing of the indicative features. Benefits can be seen especially in sensing of pressures with cardiac chambers, as pressure acquisition via catheters is hindered by overgrowth, catheter leakage, and sensor drift.

FIG. 6B is a flow diagram illustrating a second stage of the first machine learning technique of FIG. 6A, in accordance with one or more examples of the present disclosure.

The second stage, in general, refers to a process for fine-tuning the above estimation model in preparation of deployment in the medical device, which is a third stage of the first machine learning technique. As illustrated in FIG. 6A, the first stage represents the first stage of the first machine learning technique in which the above estimation model undergoes the above training process. In FIG. 6B, second stage is visualized as a process flow that determines whether the initial estimation model is sufficiently accurate to within a pre-defined degree of error and if the initial estimation model satisfies the requisite accuracy level, outputs the model as a finalized estimation model.

As described herein, the training process of machine learning based estimation models requires training data datasets from reference data provided by medical devices and/or external data sources. In addition to the variety of reference data sources, a number of factors direct the process flow of the second stage. As one example factor, different machine learning concepts may be used to generate different/alternative versions of the above estimation model. FIG. 6B illustrates machine learning methods (222), clustering algorithms (224), and regression techniques (226) as representations of the different machine learning concepts. Each resulting estimation model is evaluated for accuracy and, at the second stage, a selection is made of a best estimation model (228). In some examples, at the second stage, the fine-tuning process is to make an adjustment of an estimation model component (e.g., a parameter such as a nodal weight for a neural network) to improve upon a current metric score and/or further training.

FIG. 6B illustrates the testing/evaluating of the initial estimation model in view of one or more metrics (e.g., for assessing accuracy). The fine-tuning process of the second stage accepts, as input, the initial estimation model, and after evaluating different embodiments of that model, the process flow selects an embodiment as the finalized estimation model. As illustrated, the process flow of the second stage selects the embodiment having a highest performing estimating model for that model is automatically compiled (230) and then, deployed (e.g., installed) as an update to the medical device (232). In some examples, the update adds functionality that is new and/or an alternative/modification to existing functionality (e.g., as an improvement).

FIG. 6C is a flow diagram illustrating a third stage of the machine learning technique of FIG. 6A, in accordance with one or more examples of the present disclosure.

After implementation of the compiled model, the device is capable of using mechanical sensory feedback (242) to estimate features such as absolute maximum pressure or maximum pressure changes (244) and can be used to as reference in adjusting therapy, for example, by improving pacing slash treatment settings (246). Similar to the describe monitoring application pacing control function as well as investigatory of functions may be trained to respond to estimated pressure values by adjusting pacing settings or heart rates to improve cardiac function.

Figure 7A:
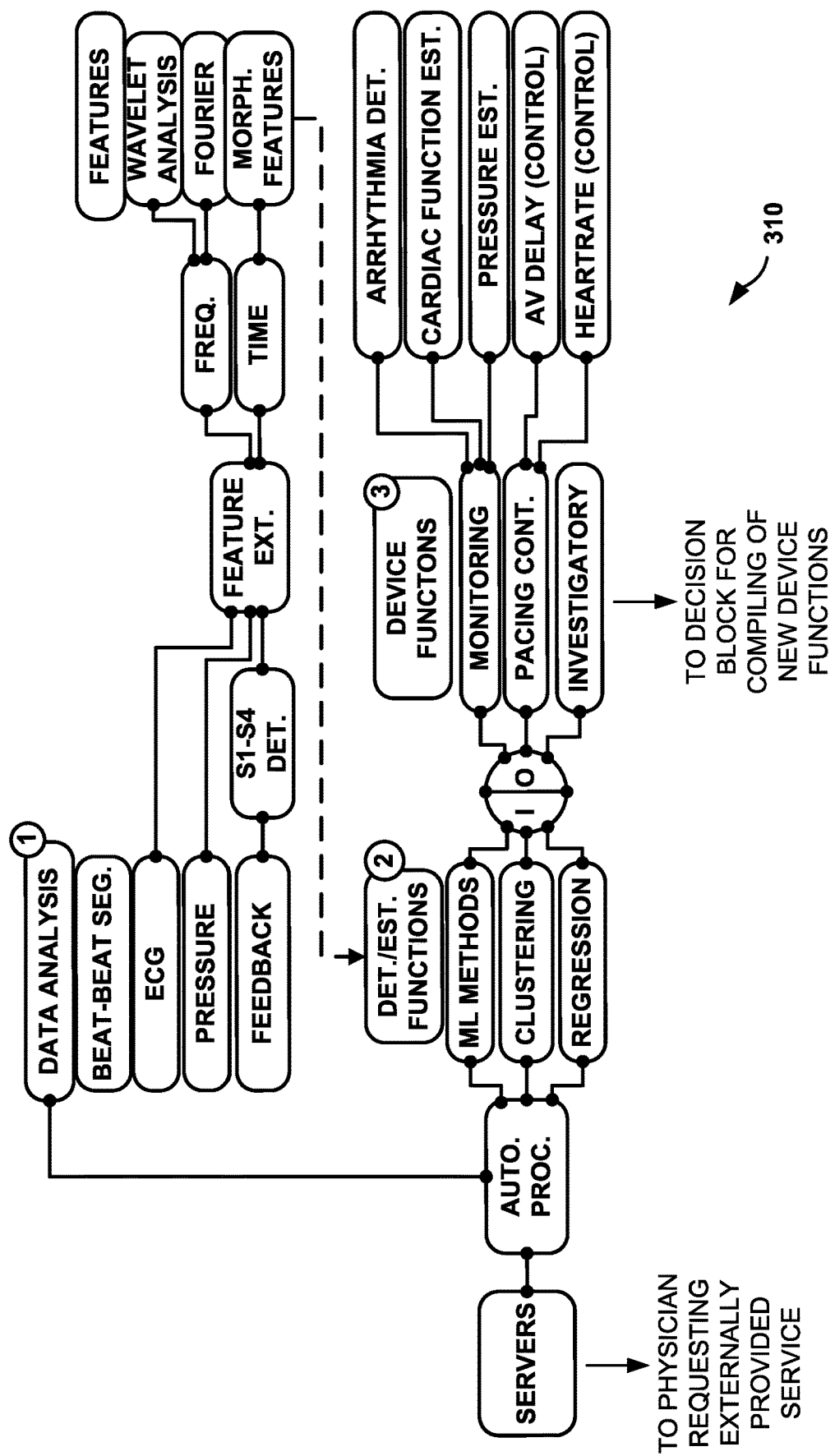
FIG. 7A is a flow diagram illustrating a first operation of a medical system running on a cloud computing environment, in accordance with one or more examples of the present disclosure.
Figure 7B:
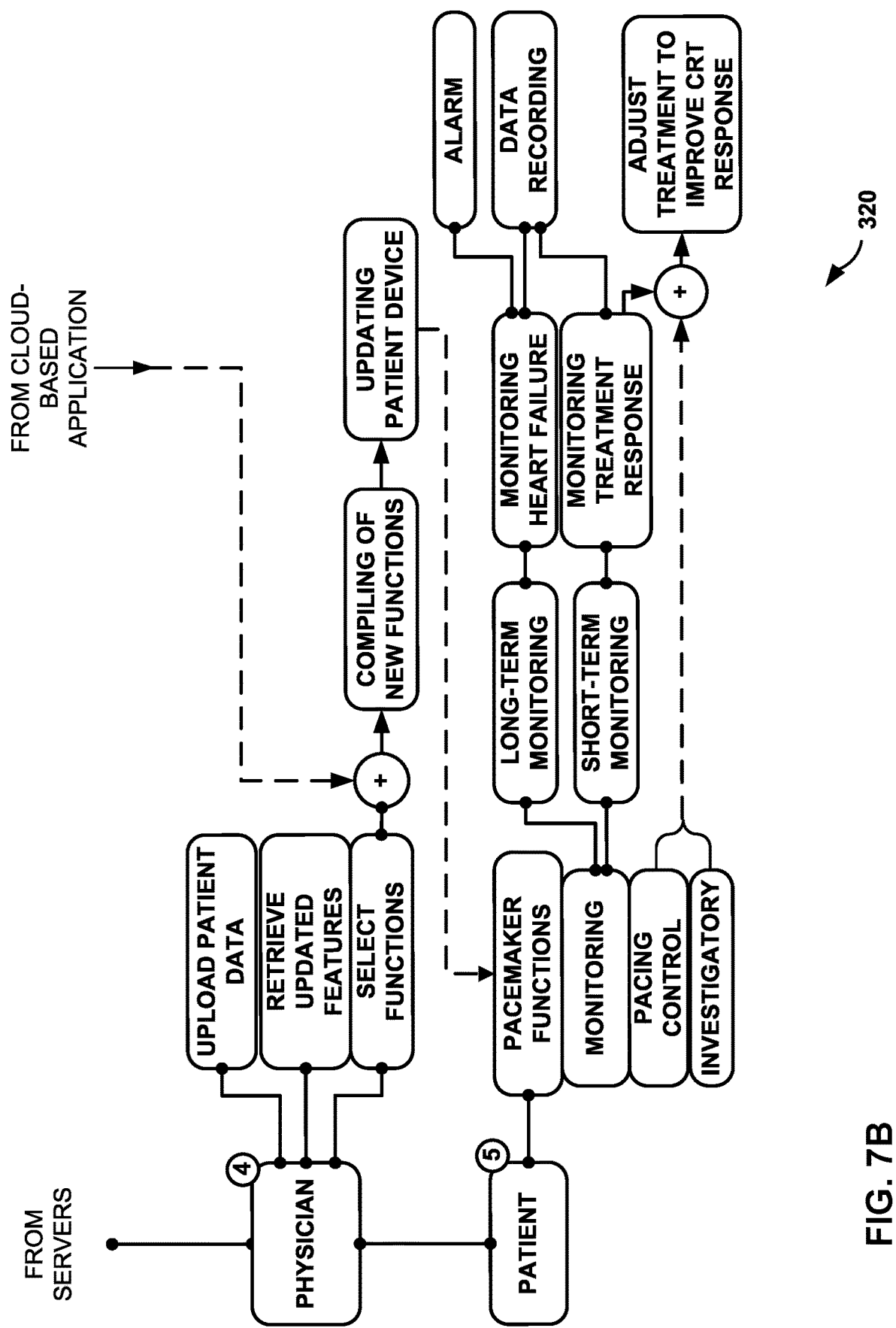
FIG. 7B is a flow diagram illustrating a second operation of the medical system of FIG. 7A, in accordance with one or more examples of the present disclosure.

FIG. 7A-7C illustrate cloud-based generation of additional medical device functionality using a second machine learning technique described herein. The medical device operates within a local environment of a patient while computing devices of the cloud (e.g., cloud computing environment) operate at a remote location and over a data network; nonetheless, the medical device and networked devices of the cloud cooperate to form a medical system also as described herein, for example, where a communication channel is generated between both devices and enables a device-backed data analysis pipeline.

FIG. 7A is a flow diagram illustrating operation 310, a first operation of a medical system running on a cloud computing environment, in accordance with one or more examples of the present disclosure. The medical system enables cloud based generation of functionality to incorporate (e.g., program) into a medical device's hardware/software for a cardiac application. The additional functionality is based on a second machine learning technique described herein.

Operation 310 represents an automated process, as described herein, to run in the cloud computing environment. Similar to the first machine learning technique of FIGS. 6A-6C, the second machine learning technique of FIGS. 7A-7C includes a training process followed by testing and then, deployment as a cardiac monitoring application (e.g., remote monitoring service 6 of FIG. 1) for a medical device. Via a communication channel between each medical device and the cardiac monitoring application, the second machine learning technique enables a device-backed data analysis pipeline.

Medical devices perform one or more functions to the benefit of their users, who may be patients receiving medical care in some form. Computing devices in the cloud computing environment operate a remote monitoring service for these medical devices and are configured to analyze cardiac activity data received from a patient's medical device. The patient, via their medical device, receives medical care and device support from a computing device in the cloud computing environment (e.g., a data center). The computing device, in accordance with operation 310, contains/manages the data submitted/acquired from that patient's medical device and other implanted medical devices.

The computing device may be configured, as a server, for executing an automated process (1) for analyzing the cardiac activity data and then, using process results to train/update an estimation model for left ventricle pressure data. For example, the computing device may receive data to analyze via the automatic automated processing pipeline described herein. In furtherance of operation 310, the computing device may perform a beat-by-beat analysis of recorded (e.g., segmented) cardiac ECG signals (e.g., regardless of data type) and extracts one or more features on a beat-by-beat basis. The computing device may program modifications into the pipeline, for example, by adding/removing features to be extracted and then, analyzed in the beat-by-beat analysis.

The computing device may configure the estimation model to provide an estimate of a measurement correlated to a sensed aspect of the patient's cardiac health. For instance, a pressure sensor within a device located near the patient's heart may directly sense left ventricle pressure data; as a substitute, the device may use the estimation model to predict the pressure data most likely to be sensed by the device. As part of the beat-by-beat analysis, the computing device receives reference data comprising sensed pressure measurements (e.g., or equivalent sensor data) generated by directly sensing the pressure in the left ventricle. The computing device compares the reference data to estimates of the same pressure measurements and based on the comparison, the computing device modifies one or more estimation model components to generate more accurate pressure estimates.

Each sensor measurement as described herein may be configured to quantify some aspect of patient activity, such that combining one or more measurements may provide a holistic view or assessment of patient health. The estimation model may be configured with any number of model components (e.g., weights, formulas, methods, and/or the like) for computing an estimate for the actual pressure within the left ventricle. After computing the pressure value, processing circuitry of the computing device compares the estimated pressure value with a baseline value. In some examples, the baseline value may be a reference value generated by a pressure sensor directly sensing left ventricle pressure data. Over time, the reference pressure values may form a range and that range corresponds to a baseline representing typical patient health or normal cardiac health for a generic patient. Deviations from the range that are either statistically significant or exceed a pre-determined threshold indicate a change in patient health. In other examples, the baseline value may be pre-determined or, as an alternative, computed using a formula and an alternative to a pressure sensor. In some examples, the baseline value represents normal health for that specific patient and any deviation from that baseline value should be evaluated. The baseline value may represent a patient's border in that the baseline value is the highest pressure value/level while still indicating no decline in that patient's health; any deviation beyond the baseline value may indicate an acute change or decline in the patient's health.

Given a breadth of available features, the computing device may execute various machine learning algorithms to generate a suitable estimation model for determining data for use in one or more cloud-based applications/services. The computing device may evaluate the reference pressure measurements to further train the estimation model. There are a number of learning algorithms for evaluating the model to determine whether the model is sufficiently trained. Supervised (e.g., linear regression) and unsupervised learning (e.g., clustering) methods may generate difference values between reference measurements and corresponding model estimates and then, graph the difference values over time to visually see changes and trends. A linear regression line could be displayed to show a general trend and based on a fitness (e.g., goodness of fit) of the regression line with the reference line, the computing device may determine a level of accuracy in the predictions generated by the model thus far. If the accuracy level indicates an accurate and therefore, sufficiently trained estimation model, for example, in terms of specificity and/or sensitivity, the computing device may generate different embodiments (2) of the same estimation model where each embodiment is a status detection function or an estimation function.

The computing device may incorporate the status detection function or the estimation function in a number of cardiac applications. The computing device may use any criteria to determine which selectable cardiac application function to use the trained estimation model as a replacement for sensor data (3). Cloud-based applications/services may employ the status detection function or estimation function to perform patient monitoring functions (e.g., using a machine learning model to estimate cardiac performance via mechanical feedback), pacing control functions (e.g., training and then, using a machine learning model to determine effective pacing settings to maximize CRT response), investigatory functions (e.g., adding an investigation of factors affecting heart failure patients such step tracking and fall detection for such patients, among others.

FIG. 7B is a flow diagram illustrating operation 320, a second operation of the medical system of FIG. 7A, in accordance with one or more examples of the present disclosure.

Operation 320 represents a device-side (e.g., client-side) application process for the medical system formed with operation 310, which is a cloud-based (e.g., server-side) application process running in the cloud computing environment. Both application processes combine to form the pipeline for adding functionality to the medical device, which is illustrated in FIGS. 7A-B.

A physician (4) provides a patient (5) with medical care. FIG. 7B illustrates the physician (4) requesting externally provided services from the cloud computing environment in which operation 310 is performed. For instance, the physician may connect the medical device to the cloud-based services and when the patient has a medical check-up, the physician may use a list of premade device features that can aid in remote monitoring and/or treatment. Via the medical device, the physician downloads one or more models and feature data to compile into that medical device. In addition, the physician may instruct the medical device to upload patient data for storage on the cloud computing environment. In some instances, the patient data may be used to further enhance the cloud-based services, for example, by enabling estimation of one or more parameters for sensed patient activity (e.g., left ventricle pressure data) without directly sensing the one or more parameters.

Operation 320 of the second machine learning technique may add new functionality or modified functionality to the medical device, which may or may not be achieved in a manner similar to FIG. 6A-6C. FIG. 7B depicts the medical device as a pacemaker and further depicts updating the pacemaker with new/modified functionality, for example, by programming one or more added functions into the pacemaker's hardware/software. Similar to FIG. 6A-6C, the new/modified pacemaker functionality being configured into the pacemaker described herein may include patient monitoring functions, pacing control functions, and investigatory functions. Additional pacemaker functions may extend (e.g., enhance) patient monitoring functionality to include therapy delivery. If the pacemaker is configured to provide the patient with treatments or some other form of therapy, the pacemaker may re-allocate those treatments and/or adjust device treatment methods in order to improve patient treatment responses.

The order and flow of the operation illustrated in FIGS. 6 and 7 are examples. In other examples according to this disclosure, more or fewer thresholds may be considered. Further, in some examples, processing circuitry may perform or not perform the methods of FIG. 6 and FIG. 7, or any of the techniques described herein, as directed by a user, e.g., via external device 24 or computing devices 100. For example, a patient, clinician, or other user may turn on or off functionality for identifying changes in patient health (e.g., using Wi-Fi or cellular services) or locally (e.g., using an application provided on a patient's cellular phone or using a medical device programmer).

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

Example 1: A medical system includes a mechanosensor configured to sense a first physiological parameter signal of a patient; and processing circuitry configured to: determine one or more features of the first physiological parameter signal; apply a machine leaning model to the one or more features of the first physiological parameter signal; and based on the application of the machine learning model, determine an estimated value of a second physiological parameter.

Example 2: The medical system of example 1, wherein the mechanosensor is configured to sense a first physiological parameter signal comprising at least one of an endocardial mechanosensory signal or an epicardial mechanosensory signal encoding heart motion data.

Example 3: The medical system of any of examples 1 and 2, wherein the mechanosensor comprises an accelerometer.

Example 4: The medical system of any of examples 1 through 3, wherein to determine the estimated value of a second physiological parameter, the processing circuitry is further configured to generate an estimate of a left-ventricular pressure measurement based on the endocardial or epicardial mechanosensory signal.

Example 5: The medical system of any of examples 1 through 4, wherein to determine the estimated value of a second physiological parameter, the processing circuitry is further configured to compute one or more derivatives of a left-ventricular pressure measurement based on the endocardial or epicardial mechanosensory signal.

Example 6: The medical system of any of examples 1 through 5, wherein to apply a machine leaning model to the one or more features of the first physiological parameter signal, the processing circuitry is further configured to apply the machine learning model to accelerometer data and, based on the application of the machine learning model, determine an estimated value of a pressure measurement in a heart chamber.

Example 7: The medical system of any of examples 1 through 6, wherein to determine an estimated value of a second physiological parameter, the processing circuitry is further configured to determine estimated pressure data.

Example 8: The medical system of any of examples 1 through 7, wherein the processing circuitry is further configured to update the machine learning model based on a comparison of the estimated value with a reference value corresponding to the second physiological parameter.

Example 9: The medical system of any of examples 1 through 8, wherein the processing circuitry is further configured to generate the machine learning model by executing a training process on a corpus of first and second physiological parameter data for a patient population or a patient sub-group.

Example 10: The medical system of any of examples 1 through 9, wherein the processing circuitry is further configured to use the estimated value of the second physiological parameter in an evaluation of cardiac synchrony.

Example 11: The medical system of any of examples 1 through 10, wherein the processing circuitry is further configured to use the estimated value of the second physiological parameter to provide therapy to correct cardiac asynchrony.

Example 12: A medical system includes communication circuitry coupled, over a network, to medical device; and processing circuitry configured to: execute a training process on a corpus of cardiac activity data for a patient population or a patient sub-group; generate a machine learning model based on the training process, wherein the machine learning model is configured to use a first physiological parameter signal to determine an estimated value of a second physiological parameter; and deploy the machine learning model for use in a medical device configured to monitor cardiac activity of a patient.

Example 13: The medical system of example 12, wherein the processing circuitry is further configured to: in response to receiving estimated left ventricle pressure measurements from the medical device, update the machine learning model by comparing the estimated left ventricle pressure measurements for a heart of the patient to reference pressure data and adjusting a component of the machine learning model based on the comparison.

Example 14: A method includes determining one or more features of a first physiological parameter signal sensed by a mechanosensor; applying a machine leaning model to the one or more features of the first physiological parameter signal; and based on the application of the machine learning model, determining an estimated value of a second physiological parameter.

Example 15: The method of example 14, wherein the mechanosensor comprises an accelerometer.

Example 16: The method of any of examples 14 and 15, wherein determining an estimated value of a second physiological parameter further comprises determining estimated pressure data.

Example 17: The method of any of examples 14 through 16, further comprising using the estimated value of the second physiological parameter in an evaluation of cardiac synchrony.

Example 18: The method of any of examples 14 through 17, further comprising using the estimated value of the second physiological parameter to provide therapy to correct cardiac asynchrony.

Example 19: The method of any of examples 14 through 18, further comprising identifying cardiac activity indicative of an abnormal cardiac rhythm based on the estimated value of the second physiological parameter.

Example 20: The method of any of examples 14 through 19, further comprising applying a therapeutic response to identified cardiac activity indicative of an abnormal cardiac rhythm based on the estimated value of the second physiological parameter.

What is claimed is:

1. A medical system comprising:
   a mechanosensor configured to sense a first physiological parameter signal of a patient, the first physiological parameter signal including at least one of an endocardial mechanosensory signal or an epicardial mechanosensory signal encoding heart motion data of a patient; and
   processing circuitry configured to:
      determine one or more features of the heart motion data of the patient;
      apply a machine leaning model to the one or more features of the heart motion data of the patient; and
      based on the application of the machine learning model, determine an estimated value of a second physiological parameter, the second physiological parameter including pressure measurement in a heart chamber.

2. The medical system of claim 1, wherein the mechanosensor comprises an accelerometer.

3. The medical system of claim 1, wherein to determine the estimated value of a second physiological parameter, the processing circuitry is further configured to generate an estimate of a left-ventricular pressure measurement based on the endocardial or epicardial mechanosensory signal.

4. The medical system of claim 1, wherein to determine the estimated value of a second physiological parameter, the processing circuitry is further configured to compute one or more derivatives of a left-ventricular pressure measurement based on the endocardial or epicardial mechanosensory signal.

5. The medical system of claim 1, wherein to apply a machine leaning model to the one or more features of the heart motion data, the processing circuitry is further configured to apply the machine learning model to accelerometer data and, based on the application of the machine learning model, determine an estimated value of a pressure measurement in a heart chamber.

6. The medical system of claim 1, wherein the processing circuitry is further configured to update the machine learning model based on a comparison of the estimated value with a reference value corresponding to the second physiological parameter.

7. The medical system of claim 1, wherein the processing circuitry is further configured to generate the machine learning model by executing a training process on a corpus of first and second physiological parameter data for a patient population or a patient sub-group.

8. The medical system of claim 1, wherein the processing circuitry is further configured to use the estimated value of the second physiological parameter in an evaluation of cardiac synchrony.

9. The medical system of claim 1, wherein the processing circuitry is further configured to use the estimated value of the second physiological parameter to provide therapy to correct cardiac asynchrony.

10. A medical system comprising:
communication circuitry coupled, over a network, to a medical device configured to monitor a first physiological parameter signal including at least one of an endocardial mechanosensory signal or an epicardial mechanosensory signal encoding heart motion data of a patient; and
processing circuitry configured to:
execute a training process on a corpus of cardiac activity data for a patient population or a patient sub-group;
generate a machine learning model based on the training process, wherein the machine learning model is configured to use the heart motion data to determine an estimated value of a second physiological parameter including pressure measurement in a heart chamber; and
deploy the machine learning model for use in the medical device.

11. The medical system of claim 10, wherein the processing circuitry is further configured to: in response to receiving estimated left ventricle pressure measurements from the medical device, update the machine learning model by comparing the estimated left ventricle pressure measurements for a heart of the patient to reference pressure data and adjusting a component of the machine learning model based on the comparison.

12. A method comprising:
determining one or more features of heart motion data included in a first physiological parameter signal sensed by a mechanosensor, the first physiological parameter signal including at least one of an endocardial mechanosensory signal or an epicardial mechanosensory signal encoding the heart motion data of a patient;
applying a machine leaning model to the one or more features of the heart motion data; and
based on the application of the machine learning model, determining an estimated value of a second physiological parameter, the second physiological parameter including pressure measurement in a heart chamber.

13. The method of claim 12, wherein the mechanosensor comprises an accelerometer.

14. The method of claim 12, further comprising using the estimated value of the second physiological parameter in an evaluation of cardiac synchrony.

15. The method of claim 12, further comprising using the estimated value of the second physiological parameter to provide therapy to correct cardiac asynchrony.

16. The method of claim 12, further comprising identifying cardiac activity indicative of an abnormal cardiac rhythm based on the estimated value of the second physiological parameter.

17. The method of claim 12, further comprising applying a therapeutic response to identified cardiac activity indicative of an abnormal cardiac rhythm based on the estimated value of the second physiological parameter.

* * * * *